(12) United States Patent
Klanner et al.

(10) Patent No.: US 7,388,106 B2
(45) Date of Patent: Jun. 17, 2008

(54) PROCESS FOR PREPARING ACROLEIN OR ACRYLIC ACID OR A MIXTURE THEREOF FROM PROPANE

(75) Inventors: Catharina Klanner, Mannheim (DE); Martin Dieterle, Mannheim (DE); Goetz-Peter Schindler, Ludwigshafen (DE); Tsung-Chieh Cheng, Heppenheim (DE); Klaus Joachim Mueller-Engel, Stutensee (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 0 days.

(21) Appl. No.: 11/533,177

(22) Filed: Sep. 19, 2006

(65) Prior Publication Data

US 2007/0088092 A1    Apr. 19, 2007

Related U.S. Application Data

(60) Provisional application No. 60/732,657, filed on Nov. 3, 2005, provisional application No. 60/729,750, filed on Oct. 25, 2005, provisional application No. 60/726,176, filed on Oct. 14, 2005.

(30) Foreign Application Priority Data

Oct. 14, 2005   (DE)  ..................  10 2005 049 699
Oct. 25, 2005   (DE)  ..................  10 2005 051 401
Nov. 3, 2005    (DE)  ..................  10 2005 052 917

(51) Int. Cl.
*C07C 27/10*   (2006.01)
*C07B 63/02*   (2006.01)

(52) U.S. Cl. .................... 562/512.2; 518/726
(58) Field of Classification Search .......... 562/512.2; 518/276
See application file for complete search history.

(56) References Cited

U.S. PATENT DOCUMENTS 6,492,548 B1 * 12/2002 Brockwell et al. .......... 562/545
7,238,827 B2    7/2007 Hechler et al.
2004/0063988 A1  4/2004 Hechler et al.
2004/0199001 A1 * 10/2004 Schindler et al. ........... 558/320
2005/0119515 A1 * 6/2005 Machhammer et al. ..... 585/658
2006/0004226 A1 * 1/2006 Machhammer et al. ..... 562/526
2006/0004227 A1 * 1/2006 Dieterle et al. ............. 562/526
2006/0004229 A1    1/2006 Dieterle et al.
2006/0258529 A1   11/2006 Diefenbacher et al.
2007/0088092 A1 * 4/2007 Klanner et al. ............. 518/726
2007/0123732 A1 * 5/2007 Dieterle et al. ............. 562/545
2007/0142689 A1 * 6/2007 Hechler et al. ............. 585/660

FOREIGN PATENT DOCUMENTS

| DE | 102 11 275 A1 | 9/2003 |
| DE | 102 45 585 A1 | 4/2004 |
| DE | 102 46 119 A1 | 4/2004 |
| DE | 10 2004 032 129 A1 | 3/2005 |
| DE | 10 2005 009 885 A1 | 9/2006 |
| DE | 10 2005 009 891 A1 | 9/2006 |
| DE | 10 2005 010 111 A1 | 9/2006 |
| DE | 10 2005 013 039 A1 | 9/2006 |
| DE | 10 2005 022 798 A1 | 11/2006 |
| WO | WO 02/055469 A1 | 7/2002 |
| WO | WO 03/078378 A1 | 9/2003 |

* cited by examiner

*Primary Examiner*—Yvonne Eyler
*Assistant Examiner*—M Louisa Lao
(74) *Attorney, Agent, or Firm*—Oblon, Spivak, McClelland, Maier & Neustadt, P.C.

(57) ABSTRACT

A process for preparing acrolein or acrylic acid or a mixture thereof from propane, in which propane is dehydrogenated under heterogeneous catalysis in a reaction zone A and the propylene formed is partially oxidized heterogeneously in a reaction zone, reaction zone A being operated in loop mode and reaction gas mixture input stream A fed to the reaction zone A comprising added molecular hydrogen which is added to this input stream as late as possible.

7 Claims, 4 Drawing Sheets

Figure 1:
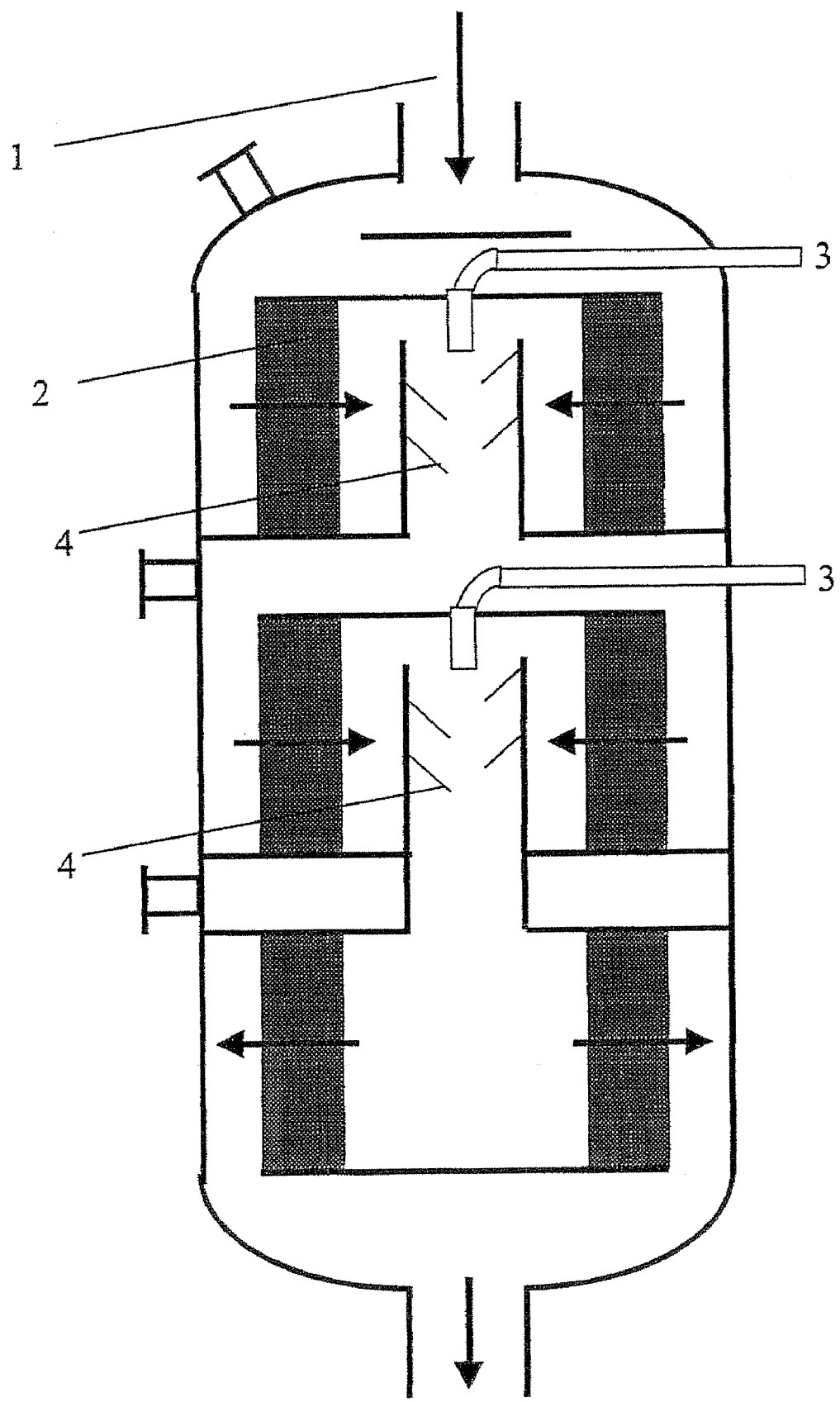

PROCESS FOR PREPARING ACROLEIN OR ACRYLIC ACID OR A MIXTURE THEREOF FROM PROPANE

The present invention relates to a process for preparing acrolein or acrylic acid or a mixture thereof from propane, in which A) a reaction gas mixture input stream A which has been obtained by combining at least four different gaseous starting streams 1, 2, 3 and 4 with the proviso that the three gaseous starting streams 1, 2 and 3 comprise propane, gaseous starting stream 4 is molecular hydrogen and gaseous starting stream 3 is fresh propane is fed to the inlet into a first reaction zone A, reaction gas mixture input stream A is conducted in reaction zone A through at least one catalyst bed over which, if appropriate with supply of further gas streams, a product gas mixture stream A comprising propane and propylene is formed by partial heterogeneously catalyzed dehydrogenation of propane, product gas mixture stream A is conducted out of the first reaction zone A by discharge therefrom and divided into two product gas mixture A substreams 1 and 2 with identical composition, and product gas mixture A substream 1, in a first cycle gas method, is recycled into the first reaction zone A as the gaseous starting stream 1, product gas mixture A substream 2 is, if appropriate, conducted into a first separating zone A in order to remove therefrom a portion or more of the constituents other than propane and propylene present therein to generate a remaining product gas mixture stream A' comprising propane and propylene, B) product gas mixture stream A substream 2 or product gas mixture stream A' are used in a secondary reaction zone B to charge at least one oxidation reactor and, in the at least one oxidation reactor, the propylene present in product gas mixture A substream 2 or in product gas mixture stream A' is subjected to a selective heterogeneously catalyzed partial gas phase oxidation with molecular oxygen to give a product gas mixture stream B comprising acrolein or acrylic acid or a mixture thereof as the target product, unconverted propane and, if appropriate, unconverted propylene, and also excess molecular oxygen, product gas mixture stream B is conducted out of reaction zone B and, in a second separating zone B, target product present in product gas mixture stream B is removed and, from the remaining residual gas comprising unconverted propane, molecular oxygen and any unconverted propylene, at least a portion comprising unconverted propane, molecular oxygen and any unconverted propylene, in a second cycle gas method, is recycled into reaction zone A as the gaseous starting stream 2 with the proviso that gaseous starting streams 2, 3 and 4 and any additional gaseous starting streams other than gaseous starting stream 1 are combined to give a gaseous motive jet mixture stream, and a jet pump which comprises a motive nozzle, a mixing zone, a diffuser and a suction nozzle is subsequently operated with the gaseous motive jet mixture stream as the motive jet, the conveying direction of the motive jet decompressed through the motive nozzle via the mixing zone and the diffuser pointing into the inlet of the first reaction zone A and the suction direction of the suction nozzle in the direction of the outlet conducting product gas mixture stream A of the first reaction zone A, and the reduced pressure generated in the suction nozzle, with division of product gas mixture stream A into the two substreams 1 and 2, sucks in product gas mixture A substream 1 and transports it through the mixing zone via the diffuser with simultaneous mixing it with the motive jet, and the reaction gas mixture input stream A formed in this way is released into the inlet of the first reaction zone A.

As a partial oxidation product of propylene, acrylic acid is a significant monomer which finds use as such or in the form of its alkyl esters for obtaining, for example, polymers suitable as adhesives or water-absorbing polymers (cf., for example, WO 02/055 469 and WO 03/078 378). Acrolein is a significant intermediate, for example for the preparation of glutaraldehyde, methionine, folic acid and acrylic acid.

Processes for preparing acrolein and/or acrylic acid, in which the propylene is obtained from propane by partial heterogeneously catalyzed dehydrogenation and, in the presence of unconverted (inert) propane, subjected as a constituent of a partial oxidation mixture to a heterogeneously catalyzed partial gas phase oxidation with molecular oxygen to give product mixtures comprising acrolein and/or acrylic acid, are known (cf., for example, DE-A 102 45 585 and the prior art cited in this document).

In contrast to the exothermic heterogeneously catalyzed oxydehydrogenation, which is forced by oxygen present and in which free hydrogen is neither formed as an intermediate (the hydrogen pulled from the propane to be dehydrogenated is pulled out directly as water ($H_2O$)) nor is detectable, a heterogeneously catalyzed dehydrogenation shall be understood in this document to mean a (conventional) dehydrogenation whose thermal character, in contrast to the oxydehydrogenation, is endothermic (an exothermal hydrogen combustion may be included in the heterogeneously catalyzed dehydrogenation as a subsequent step) and in which free molecular hydrogen is formed at least as an intermediate. This generally requires different reaction conditions and different catalysts than the oxydehydrogenation.

In a corresponding manner, fresh propane in this document is understood to mean propane which has participated neither in a dehydrogenation in reaction zone A nor in a partial oxidation of propylene to acrolein and/or acrylic acid in reaction zone B. It has preferably not participated in any chemical reaction at all. In general, it is supplied in the form of crude propane which preferably fulfills the specification according to DE-A 102 46 119 and DE-A 102 45 585, and which normally also comprises components other than propane in small amounts. Such crude propane is obtainable, for example, by processes described in DE-A 10 2005 022 798. Normally crude propane comprises propane to an extent of at least ≧90% by weight and preferably to an extent of at least ≧95% by weight.

Typically, the prior art processes addressed above are carried out in such a way that, from the residual gas which remains after the target product removal from the product gas mixture of the partial oxidation and comprises unconverted propane, molecular oxygen and, if appropriate, unconverted propylene, at least a portion comprising unconverted propane, molecular oxygen and any unconverted propylene is recycled in cycle gas mode into the heterogeneously catalyzed dehydrogenation.

It has already been proposed (for example DE-A 10 2004 032 129 and DE-A 10 2005 013 039) that a mixture of steam, fresh propane and such cycle gas be fed as reaction gas mixture input gas to the heterogeneously catalyzed dehydrogenation of propane to propylene. The heterogeneously catalyzed propane dehydrogenation should appropriately be implemented in the form of a tray reactor in which the catalyst beds are favorably arranged in radial or axial succession. Appropriately, in such a tray reactor, the fixed catalyst bed type is employed. Advantageously, the number of catalyst bed trays in such a tray reactor is three. The prior art recommends performing the heterogeneously catalyzed partial propane dehydrogenation autothermally. To this end, molecular oxygen (for example in the form of air) is added to a restricted extent to the reaction gas mixture beyond the first catalyst bed passed through and between the (fixed) catalyst beds which follow the first (fixed) catalyst bed in flow direction. For example, generally catalyzed by the dehydrogenation catalysts themselves, restricted combustion of molecular hydrogen formed in the course of the heterogeneously catalyzed propane dehydrogenation (and also, if appropriate, of propane to a minor extent at most) can be brought about, whose exothermicity substantially retains the dehydrogenation temperature (adiabatic reactor configuration).

In comparative examples 1, 3 and 4 of DE-A 10 2004 032 129 and in the working example of DE-A 10 2005 010 111, a heterogeneously catalyzed partial propane dehydrogenation as described above is simulated in a tray reactor (3 catalyst bed trays) by three dehydrogenation tubular reactors connected in series. Instead of such a series connection of tubular reactors, it is also possible in these comparative examples or in this working example to use an (adiabatic) tray reactor according to the accompanying FIGS. 1 and 2 (with 3 fixed catalyst bed trays in each case).

In the tray reactor type according to FIG. 1, the catalyst bed (2) is in each case flowed through from the outside inward. In contrast, in the tray reactor type according to FIG. 2, the particular catalyst bed (2) is flowed through from the inside outward. The addressed (1) in each case represent reaction gas mixture input gas, (3) shows the air feed and (4) are mixing elements.

Otherwise, the following reactor data, based on a propane flow of 72 280 kg/h in the reaction gas mixture input gas, and a total air feed of 3496 kg/h are appropriate:

| FIG. 1 reactor: | |
|---|---|
| Total catalyst mass in the reactor = | 30 t |
| Catalyst mass per tray = | 10 t |
| Height of the catalyst bed per tray = | 5.47 m |
| Bulk density of each catalyst bed = | 1200 kg/m³ |
| Inner radius of catalyst bed = | 1.05 m |
| Outer radius of catalyst bed = | 1.26 m |
| Volume of the catalyst bed per tray = | 8.33 m³ |
| Diameter of the inlet tube = | 1.4 m |
| Reactor internal diameter = | 3.2 m |
| Reactor height of cylindrical section (without hoods) = | 21 m |
| Number of mixing elements = | 2 |
| Entrance pressure of the reaction mixture input gas = | 3.1 bar abs. |

The catalyst to be used in each case is the catalyst of the corresponding comparative example or of the working example. The same applies to the reaction temperatures and the composition of the reaction gas mixture input gas.

Preferred reactor construction material for all reactor parts is appropriately Si-containing stainless steel or steel, for example that of the 1.4841 type.

Figure 2:
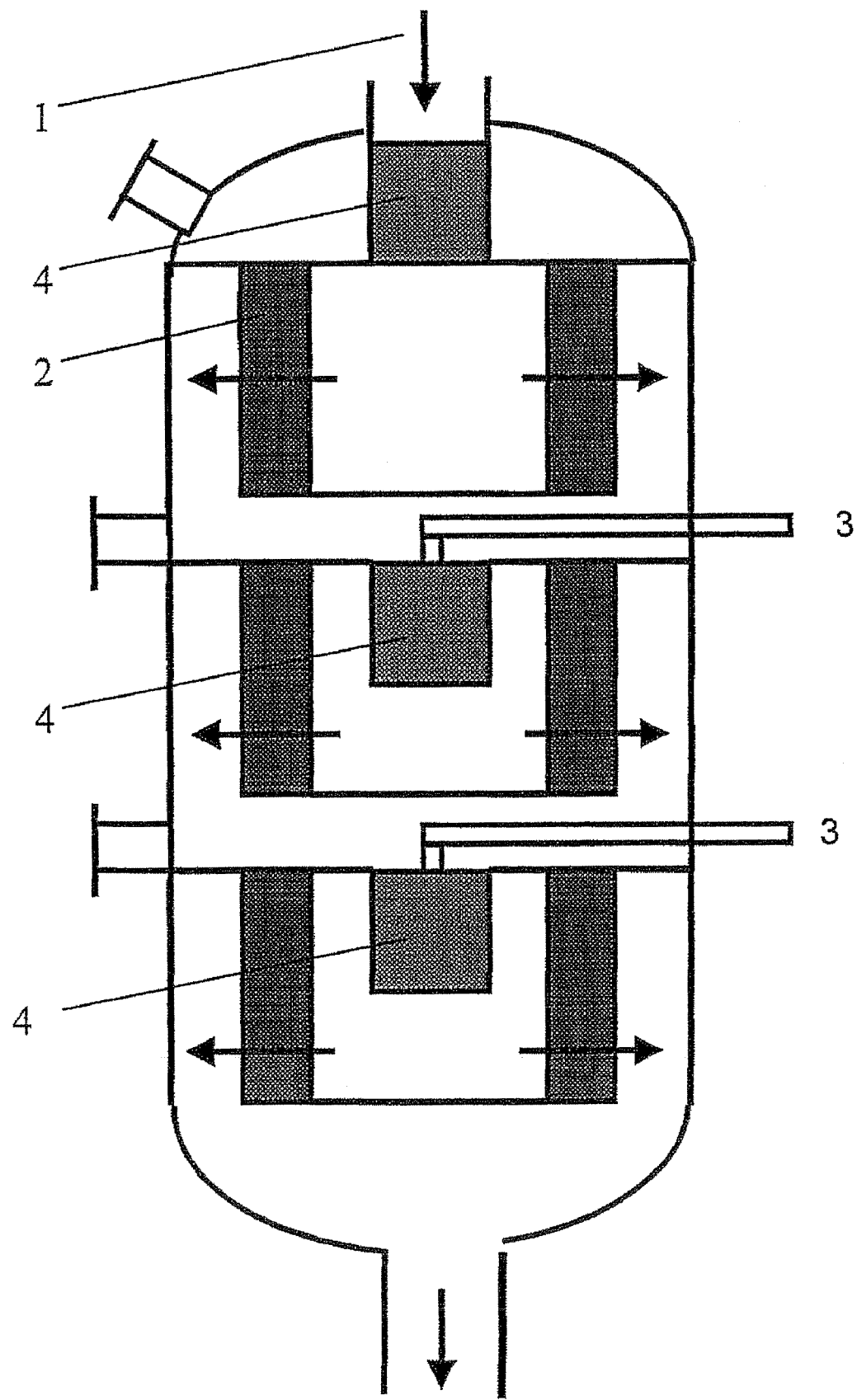

| FIG. 2 reactor: | |
|---|---|
| Total catalyst mass in the reactor = | 30 t |
| Catalyst mass per tray = | 10 t |
| Height of the catalyst bed per tray = | 4.84 m |
| Bulk density of each catalyst bed = | 1200 kg/m³ |
| Inner radius of catalyst bed = | 1.2 m |
| Outer radius of catalyst bed = | 1.41 m |
| Volume of the catalyst bed per tray = | 8.33 m³ |
| Diameter of the inlet tube = | 1.4 m |
| Reactor internal diameter = | 3.4 m |
| Reactor height of cylindrical section (without hoods) = | 19 m |
| Number of mixing elements = | 2 |
| Entrance pressure of the reaction mixture input gas = | 3.1 bar abs. |

The catalyst to be used in each case is the catalyst of the corresponding comparative example or of the working example. The same applies to the reaction temperatures and the composition of the reaction gas mixture input gas. Preferred reactor construction material for all reactor parts is appropriately Si-containing stainless steel or steel, for example that of the 1.4841 type.

Appropriately, the partial heterogeneously catalyzed dehydrogenation of propane is substantially operated, divided between the three catalyst trays, in such a way that the conversion of the propane conducted into the reactor, based on single reactor pass, is approx. 20 mol %. The selectivity of propylene formation achieved is regularly 90 mol %. The maximum contribution of a single tray to the conversion migrates from the front backward in flow direction with increasing operating time. In general, the catalyst charge is regenerated before the third tray in flow direction provides the maximum contribution to the conversion. Advantageously, the regeneration is effected when the carbonization of all trays has attained an identical extent.

It is quite generally favorable for the above-described heterogeneously catalyzed partial dehydrogenation of propane when the loading on the total amount of catalyst (sum over all beds) with the total amount of propane and propylene is $\geq$500 l (STP)/l·h and $\geq$20000 l (STP)/l·h (typical values are from 1500 l (STP)/l·h to 2500 l (STP)/l·h). The maximum reaction temperature within an individual fixed catalyst bed is advantageously kept at from 500° C. to 600° C. Particularly advantageously, the reaction gas mixture input gas in the above-described heterogeneously catalyzed partial propane dehydrogenation stage in the tray reactor consists merely of fresh propane and the cycle gas which has been recycled from the partial oxidation into the dehydrogenation and, stemming from the partial oxidation, comprises a sufficient amount of steam to result in a satisfactory lifetime of the dehydrogenation catalyst beds. In other words, the comparative examples and the example can be carried out in this way in the tray reactors described even when the addition of the extra steam in the dehydrogenation is dispensed with. Otherwise, the statements made on such procedures in DE-A 10 2005 009 885, DE-A 10 2005 010111, DE-A 10 2005 009 891, DE-A 10 2005 013 039 and DE-A 10 2004 032 129 apply. In this document too, the loading of a catalyst bed catalyzing one reaction step with reaction gas mixture is understood to mean the amount of reaction mixture in standard liters (=l (STP); the volume in liters that the appropriate amount of reaction gas mixture would take up under standard conditions (0° C., 1 bar)) which is conducted through one liter of catalyst bed (e.g. fixed catalyst bed) per hour. However, the loading may also be based only on a constituent of the reaction gas mixture. In that case, it is the amount of this constituent in l (STP)/l·h which is conducted through one liter of catalyst bed per hour (pure inert material beds are not counted in the fixed catalyst bed).

The loading may also be based only on the amount of catalyst present in a catalyst bed which may comprise the actual catalyst diluted with inert material (in that case, this is stated explicitly).

A disadvantage of the prior art process described is that virtually all catalysts which catalyze the dehydrogenation of propane also catalyze the combustion (full oxidation of propane and propylene to carbon oxides and steam) of propane and propylene with molecular oxygen, but molecular oxygen is normally already present in the cycle gas from the partial oxidation which is recycled into the heterogeneously catalyzed partial dehydrogenation of propane. This is because, for reasons of an increased catalyst lifetime in the heterogeneously catalyzed partial oxidation, molecular oxygen, measured by the stoichiometry of the partial oxidation, is normally used in excess. The catalyzed combustion reaction of this molecular oxygen with propane and/or propylene present in the reaction mixture input gas reduces the selectivity of propylene formation in the heterogeneously catalyzed partial propane dehydrogenation.

It has therefore already been proposed (see DE-A 102 11 275), in a multistage preparation of acrolein and/or acrylic acid from propane, to perform the heterogeneously catalyzed partial propane dehydrogenation in such a way that the product gas withdrawn from the dehydrogenation zone is divided into two portions of identical composition in order to feed only one of the two portions to the partial oxidation, while the other portion is recycled into the dehydrogenation as a constituent of the reaction gas mixture input gas. The molecular hydrogen present in this cycle gas coming from the dehydrogenation itself is then intended to protect the propane and, if appropriate, propylene present in the reaction gas mixture input gas from the molecular oxygen which is likewise present in this input gas. This protection is based on the fact that the combustion, normally catalyzed heterogeneously by the same catalysts, of molecular hydrogen to water is preferred kinetically over the full combustion of propane and/or propylene.

DE-A 102 11 275 also already discloses the conduction of dehydrogenation cycle gas by means of the jet pump principle (it is also referred to as loop mode). This document also addresses the possibility of adding molecular hydrogen additionally to the reaction gas mixture in the propane dehydrogenation. DE-A 102 11 275 makes no statement on the requirement to meter the molecular hydrogen into the motive jet for the jet pump in a certain feed hierarchy.

DE-A 10 2004 032 129 and DE-A 10 2005 013 039 propose not undertaking the recycling of the cycle gas which comprises molecular oxygen and stems from the heterogeneously catalyzed partial oxidation into the reaction gas mixture input gas for the heterogeneously catalyzed partial propane dehydrogenation. Instead, the recycling into the reaction gas mixture of the dehydrogenation should not be effected until a certain dehydrogenation conversion. DE-A 10 2004 032 129 too also proposes adding external molecular hydrogen additionally to the reaction gas mixture of the dehydrogenation prior to this recycling. In addition, DE-A 10 2004 032 129 also propagates the loop mode for the hydrogenation. In this case, motive jet is exclusively the cycle gas recycled from the partial oxidation into the dehydrogenation.

This operating mode is disadvantageous in that the externally metered molecular hydrogen in this case is still conducted in a significant portion as a constituent of the product gas mixture from the dehydrogenation into the partial oxidation without its protective potential having been utilized comprehensively. In addition, the jet pump also brings the portion of the product gas mixture from the partial dehydrogenation to an elevated pressure which is released into the partial oxidation. Prior to the partial oxidation, however, an additional compression of the appropriate reaction gas mixture starting gas by means of a separate compressor is normally required in each case in order to balance out the pressure drop associated with the partial oxidation. In general, the conversion of the product gas mixture A substream 2 into the product gas mixture stream A' is also carried out under pressure. Against this background, pressure stress, attendant in the way described, on the jet pump is of little purpose.

Against this background, DE-A 10 2005 009 885 recommends, in working example II, a loop mode in which the reaction gas mixture input gas for the heterogeneously catalyzed partial dehydrogenation of propane is composed of cycle gas which is recycled from the partial oxidation and is composed of fresh propane, of external molecular hydrogen, of a minimum amount of external steam and cycle gas recycled from the dehydrogenation itself (it would also be possible to dispense with the external steam). The motive jet used is a mixture of fresh propane, external molecular hydrogen, cycle gas from the partial oxidation and external steam. With regard to any metering sequence to be observed in generating the motive jet, DE-A 10 2005 009 885 makes no statement. This is because the applicant at that time, at which the stainless steel pilot plant operated was new, had no indications of the requirement for a specific metering sequence. Since then, however, it has been found that, in the course of prolonged operating time, fly rust which forms in the smallest amounts in plants made of stainless steel or made of conventional steel (i.e. generally made of steel) catalyzes the combustion of molecular hydrogen with molecular oxygen. This is disadvantageous in that the heat of combustion formed at least partly does not come into effect where it is required, specifically in the endothermic dehydrogenation. Instead, even in the case of the desired adiabatic dehydrogenation, it is lost at least partly since an ideal adiabatic reaction apparatus cannot be realized. This either causes the necessity of supplying external heat, which is associated generally with undesired cracking processes of the hydrocarbons involved on the heat transfer surfaces, or results in dehydrogenation conversions which are significantly reduced. Both are disadvantageous.

It was therefore an object of the present invention to provide an improved process for preparing acrolein or acrylic acid or a mixture thereof from propane, which either no longer has the disadvantages described or at worst has them only in reduced form.

Accordingly, a process has been found for preparing acrolein or acrylic acid or a mixture thereof from propane, in which A) a reaction gas mixture input stream A which has been obtained by combining at least four different gaseous starting streams 1, 2, 3 and 4 with the proviso that the three gaseous starting streams 1, 2 and 3 comprise propane, gaseous starting stream 4 is molecular hydrogen and gaseous starting stream 3 is fresh propane is fed to the inlet into a first reaction zone A, reaction gas mixture input stream A is conducted in reaction zone A through at least one catalyst bed over which, if appropriate with supply of further gas streams, a product gas mixture stream A comprising propane and propylene is formed by partial heterogeneously catalyzed dehydrogenation of propane, product gas mixture stream A is conducted out of the first reaction zone A by discharge therefrom and divided into two product gas mixture A substreams 1 and 2 with identical composition, and product gas mixture A substream 1, in a first cycle gas method, is recycled into the first reaction zone A as the gaseous starting stream 1, product gas mixture A substream 2 is, if appropriate, conducted into a first separating zone A in order to remove therefrom a portion or more of the constituents other than propane and propylene present therein to generate a remaining product gas mixture stream A' comprising propane and propylene, B) product gas mixture stream A substream 2 or product gas mixture stream A' are used in a secondary reaction zone B to charge at least one oxidation reactor and, in the at least one oxidation reactor, the propylene present in product gas mixture A substream 2 or in product gas mixture stream A' is subjected to a selective heterogeneously catalyzed partial gas phase oxidation with molecular oxygen to give a product gas mixture stream B comprising acrolein or acrylic acid or a mixture thereof as the target product, unconverted propane and, if appropriate, unconverted propylene, and also excess molecular oxygen, product gas mixture stream B is conducted out of reaction zone B and, in a second separating zone B, target product present in product gas mixture stream B is removed and, from the remaining residual gas comprising unconverted propane, molecular oxygen and any unconverted propylene, at least a portion comprising unconverted propane, molecular oxygen and any unconverted propylene, in a second cycle gas method, is recycled into reaction zone A as the gaseous starting stream 2 with the proviso that gaseous starting streams 2, 3 and 4 and any additional gaseous starting streams other than gaseous starting stream 1 are combined to give a gaseous motive jet mixture stream, and a jet pump which comprises a motive nozzle, a mixing zone, a diffuser and a suction nozzle is subsequently operated with the gaseous motive jet mixture stream as the motive jet, the conveying direction of the motive jet decompressed through the motive nozzle via the mixing zone and the diffuser pointing into the inlet of the first reaction zone A and the suction direction of the suction nozzle in the direction of the outlet conducting product gas mixture stream A of the first reaction zone A, and the reduced pressure generated in the suction nozzle, with division of product gas mixture stream A into the two substreams 1 and 2, sucks in product gas mixture A substream 1 and transports it through the mixing zone via the diffuser with simultaneous mixing it with the motive jet, and the reaction gas mixture input stream A formed in this way is released into the inlet of the first reaction zone A, wherein gaseous starting streams 2 and 3 and any additional gaseous starting streams other than gaseous streams 1 and 4 are first combined in any sequence to give a gaseous starting mixture stream and gaseous starting stream 4 is only then added to the gaseous starting mixture stream to form the gaseous motive jet mixture stream.

Apart from the characterizing part, the process according to the invention can be carried out like the corresponding processes described in the documents EP-A 117 146, U.S. Pat. No. 3,161,670, DE-A 33 13 573, WO 01/96 270, DE-A 103 160 39, DE-A 10 2005 013 039, DE-A 10 2004 032 129, DE-A 102 11 275, DE-A 102 45 585, DE-A 10 2005 009 891, DE-A 10 2005 010 111, DE-A 10 2005 022 798 and DE-A 10 2005 009 885.

Preferably in accordance with the invention, the gaseous starting stream 4 is added to the gaseous starting mixture stream (to form the motive jet mixture stream) within a minimum time. In addition, the gaseous starting stream 4 is added to the gaseous starting mixture stream (to form the motive jet mixture stream) in such a way that, from the time of formation of the motive jet mixture stream to the time at which reaction gas mixture input stream A reaches the first catalyst bed of reaction zone A (in flow direction) comprising dehydrogenation catalyst, not more than 30 seconds elapse, preferably not more than 20 or than 10 seconds, advantageously not more than 7 seconds, more preferably not more than 5 seconds, even more preferably not more than 3 seconds and at best not more than 1 or 0.5 or 0.1 second.

Useful processes for removing target product present in product gas mixture stream B for the process according to the invention are in principle all processes known in this regard in the prior art. They essentially feature the conversion of the target product from the gaseous into the condensed phase, for example by absorptive and/or condensative methods. Useful absorbents are, for example, water, aqueous solution and/or organic solvents. In the context of this "condensation" of the target product, a residual gas which is not transferred to the condensed phase normally remains, which comprises the constituents of the product gas mixture stream B which are comparatively difficult to condense. These are typically in particular those components whose boiling point at standard pressure (1 bar) is $\leq -30°$ C. (their total proportion in the residual gas is generally $\geq 70\%$ by volume, frequently $\geq 80\%$ by volume and in many cases $\geq 90\%$ by volume). These include primarily unconverted propane, excess molecular oxygen remaining in product gas mixture stream B and any unconverted propylene. In addition, the residual gas will generally comprise inert diluent gases, for example $N_2$, $CO_2$, noble gases (He, Ne, Ar, etc.), CO, and also, to a minor extent, acrylic acid, acrolein and/or $H_2O$ (the steam content in the residual gas may be up to 25% by volume, frequently up to 20% by volume, or up to 10% by volume, but in many cases also below 10% by volume or below 5% by volume). This aforementioned residual gas (based on the amount of propane present therein) normally forms the majority (typically at least 80%, or at least 90%, or at least 95% or more) of the residual gas formed in separation zone B and is therefore referred to in this document, inter alia, also as main residual gas.

According to the invention, at least a portion of this residual gas which comprises unconverted propane, molecular oxygen and any unconverted propylene (main residual gas), in cycle gas mode, is normally recycled into reaction zone A as the gaseous starting stream 2. Appropriately in accordance with the invention, the entirety of this residual gas is recycled as the gaseous starting stream 2 into reaction zone A.

Especially when the condensation of the target product is effected by absorption by means of an organic solvent, at least one second residual gas comprising unconverted propane and any unconverted propylene is generally obtained in separation zone B (based on propane present therein, its amount is normally substantially smaller in comparison to the amount of main residual gas). This is attributable to the condensed phase which forms also taking up unconverted propane and any unconverted propylene to a certain extent.

In the further course of the extractive, distillative, crystallizative and/or desorptive removal of the target product from the condensed phase, this unconverted propane and any propylene is normally recovered as a constituent of at least one further gas phase and, in the process according to the invention, preferably likewise recycled into reaction zone A.

This can be done, for example, in a mixture with the main residual gas (in that case, referred to in this document as overall residual gas). However, it can also be done in the form of gas streams to be recycled independently into reaction zone A. It will be appreciated that this recycling into reaction zone A can also be effected as a further gaseous starting stream. These gas streams to be recycled independently may be free of oxygen or else comprise oxygen (secondary residual gas) (for example when it is obtained by stripping by means of air or at the top of a rectification column flushed by means of air as a polymerization inhibitor).

In the context of this invention, main residual gas, overall residual gas and secondary residual gas form residual gas which comprises unconverted propane, molecular oxygen and any unconverted propylene and can be recycled into reaction zone A as gaseous starting stream 2. According to the invention, molecular oxygen-free residual gas which is obtained in separation zone B and comprises unconverted propane and any unconverted propylene can be recycled into reaction zone A in a mixture with main residual gas and/or secondary residual gas (i.e., for example, as a constituent of overall residual gas), for example as a constituent of gaseous starting stream 2 and/or independently (in this case, the residual gas is not residual gas recycled in reaction zone A in the context of the invention). In the latter case, this recycling can be effected without any restriction, i.e., for example, even as a further gaseous starting stream. Especially when substantially all constituents other than propane and propylene present in product gas mixture A substream 2 are removed therefrom in a first separation zone A in the process according to the invention and the resulting product gas mixture stream A' is used to charge the at least one oxidation reactor, substantially the entirety of the gas streams which comprise unconverted propane and any unconverted propylene and are obtained in separation zone B will, in the process according to the invention, be recycled into reaction zone A, preferably as a constituent of overall residual gas as the gaseous starting stream 2. However, it would also be possible if appropriate to use portions (as described, for example in DE-A 10 2004 032 129) for other purposes, for example for energy generation and/or synthesis gas preparation and/or as a diluent gas in reaction zone B. In general, in the above-described case, however, at least half or two thirds (i.e. 50% by volume or 66.6% by volume), preferably at least three quarters and most preferably the entirety of the aforementioned residual gas obtained in separation zone B (in each case individually with regard to the main and/or secondary or overall residual gas) will be recycled into reaction zone A, preferably in accordance with the invention as a constituent of gaseous starting stream 2. When only one residual gas stream comprising unconverted propane, molecular oxygen and unconverted propylene is obtained in separation zone B (this is frequently the general case), it is, especially when substantially all constituents other than propane and propylene present in product gas mixture A substream 2 are removed therefrom in a first separating zone in the process according to the invention and the resulting product gas mixture stream A' is used to charge at least one oxidation reactor, recycled preferably fully in accordance with the invention (if appropriate minus a portion of identical composition conducted as diluent gas into reaction zone B) into reaction zone A as gaseous starting stream 2. It can then also be divided into two portions of identical composition and, as described above, only one portion is recycled into reaction zone A as gaseous starting stream 2 and the other portion used further in another way. When more than one such residual gas stream is obtained in separation zone B, these residual gas streams (as already mentioned) may, in accordance with the invention, be recycled together (for example combined) in reaction zone A as gaseous starting stream 2. It will be appreciated that the recycling of these residual gas streams into reaction zone A can also be effected individually. It is also possible for a portion of the residual gas to be recycled into reaction zone A not as gaseous starting stream 2 but rather not until along the reaction path of the heterogeneously catalyzed dehydrogenation of propane in reaction zone A. The reaction path of the heterogeneously catalyzed dehydrogenation of propane in the first reaction zone A shall be understood to mean the flow path of the propane present in the reaction gas mixture input stream A through reaction zone A as a function of the dehydrogenating conversion (the conversion in the heterogeneously catalyzed dehydrogenation) of this propane.

Residual gas recycled into reaction zone A as gaseous starting stream 2 in the process according to the invention normally consists to an extent of $\geq 70\%$ by volume, frequently to an extent of $\geq 80\%$ by volume and in many cases to an extent of $\geq 90\%$ by volume, usually to an extent of $\geq 95\%$ by volume or to an extent of $\geq 98\%$ by volume of constituents whose boiling point at standard pressure (1 bar) is $\leq -30°$ C.

Especially when substantially all constituents other than propane and propylene present in product gas mixture A substream 2 are removed therefrom in a first separation zone A in the process according to the invention and the resulting product gas mixture stream A' is used to charge at least one oxidation reactor, the composition of the gaseous starting stream 2 comprises typically:

from 0 to 2% by volume, in many cases from 0 to 1% by volume, frequently from 0 to 0.5% by volume of propene;

from 0 to 2% by volume, in many cases from 0 to 1% by volume, frequently from 0 to 0.5% by volume of acrolein;

from 0 to 0.5% by volume, in many cases from 0 to 0.1% by volume, frequently from 0 to 0.05% by volume of acrylic acid;

from 0 to 4% by volume, in many cases from 0 to 2% by volume, frequently from 0 to 1.5% by volume of $CO_x$;

from 10 to 50% by volume, in many cases from 20 to 30% by volume of propane;

from 0 to 70% by volume, in many cases from 40 to 70% by volume of $N_2$;

from 1 to 10% by volume, in many cases from 2 to 5% by volume, frequently from 2.5 to 3.5% by volume of $O_2$ and from >0 to 15% by volume of $H_2O$.

Frequently, the gaseous starting stream 2 in the process according to the invention has a temperature of from 50 to 200° C., or from 70 to 130° C., and a pressure of from 1.5 to 5 bar, preferably from 3 to 4 bar.

Typical temperatures for the gaseous starting stream 3 are from 0 to 50° C., frequently from 5 to 20° C., at pressures of from 3 to 6 bar or from 4 to 5 bar.

In the inventive procedure, the gaseous starting stream 4 has to be "molecular hydrogen". This shall be understood in this document to mean gas streams which either consist only of molecular hydrogen or which consist to an extent of at least 50% by volume, preferably to an extent of at least 60% by volume, or to an extent of at least 70% by volume, or to an extent of at least 80% by volume, or to an extent of at least 90% by volume, or to an extent of at least 95% by volume or to an extent of at least 98% by volume or to an extent of at least 99% by volume of molecular hydrogen and, in the particular remaining amount, of an inert gas. In this document, inert gas shall be understood quite generally to mean a reaction gas constituent which behaves substantially inertly under the conditions of the appropriate reaction (in the aforementioned case that of the heterogeneously catalyzed dehydrogenation) and, each inert reaction gas constituent taken alone, remains chemically unchanged to an extent of more than 95 mol %, preferably to an extent of more than 99 mol %. Examples of such inert gases are $N_2$, noble gases, $CO_2$ or else steam.

Appropriately in accordance with the invention, the gaseous starting stream 4 in the process according to the invention has a temperature of from 20 to 100° C., frequently from 40 to 60° C., and a pressure in the range from 1 to 5 bar.

An advantageous process according to the invention is one in which from 60 to 90 mol %, preferably from 75 to 85 mol % of the molecular hydrogen present in reaction gas mixture input stream A stems from product gas mixture A substream 1 (gaseous starting stream 1) and the remaining from 10 to 40 mol % or from 15 to 25 mol % from the gaseous starting stream 4.

Useful gaseous starting streams over and above gaseous starting streams 1 to 4 are especially steam or spray mist consisting of fine water droplets. Appropriately, such a starting stream 5 composed of steam, for example in gaseous form, has a temperature of from 100 to 200° C., frequently from 120 to 160° C., and a pressure of from 1 bar to 4 bar.

According to the invention, such a gaseous starting stream 5 consisting of steam will be integrated in the process according to the invention in the gaseous starting mixture stream before gaseous starting stream 4 is added to the latter.

The aforementioned integration is effected appropriately in such a way that first gaseous starting stream 5 is added to gaseous starting stream 2 and gaseous starting stream 3 is added to the resulting gaseous mixture.

The resulting starting mixture stream is advantageously only then conducted through an indirect heat exchanger in order to cool product gas mixture A substream 2 (for example from 500 to 600° C. down to 150 to 350° C.) and simultaneously to heat the starting stream (for example from 20 to 200° C. up to 350 to 530° C.) therein. The presence of steam reduces the risk of carbonization associated with the heating. Thereafter, the purification required in accordance with the invention of the gaseous starting stream 4 with the starting mixture stream brought to temperature as desired is effected to form the motive jet mixture stream. Advantageously in accordance with the invention, the latter has a temperature of from 350 to 550° C. and a pressure of from 2 to 5 bar.

The additional use of steam as the gaseous starting steam 5 is especially advantageous for the catalyst lifetime in the heterogeneously catalyzed partial dehydrogenation, as is yet to be described below. Advantageously in accordance with the invention, however, the additional use of such a gaseous starting stream 5 will as far as possible be dispensed with to leave the steam which stems from the formation of water of reaction proceeding in the partial oxidation and is present advantageously in gaseous starting stream 2. Steam contents in reaction gas mixture input stream A of from 1 to 20 or to 15 or to 10% by volume, frequently from 4 to 6% by volume, have been found to be appropriate in accordance with the invention.

Especially when, in the process according to the invention, product gas mixture A substream 2 is used, in a variant less preferred in accordance with the invention, as such to charge the at least one oxidation reactor, it is appropriate in accordance with the invention to remove at least a portion of the constituents other than propane, molecular oxygen and any propylene present in the residual gas obtained in separation zone B therefrom before it is employed to form gaseous starting stream 2.

Appropriate removals are described, for example, in EP-A 117 146, U.S. Pat. No. 3,161,670, DE-A 33 13 573, DE-A 103 16 039 and in DE-A 102 45 585.

For the process according to the invention, it is appropriate in the context of the loop mode to be employed in reaction zone A when the amount of product gas mixture A substream 1, based on the total amount of product gas mixture stream A, is from 25 to 75% by volume or from 30 to 70% by volume, advantageously from 40 to 60% by volume and more preferably 50% by volume.

The propane conversion in the pass of the reaction gas mixture input stream A, which is constituted preferably in accordance with the invention merely of gaseous starting streams 1, 2, 3 and 4 and, if appropriate, a gaseous starting stream 5 of steam, may, in the process according to the invention, (based on single pass of reaction gas mixture input stream A through reaction zone A and based on the total amount of fresh propane present in reaction gas mixture input stream A and propane stemming from gaseous starting stream 2) be from 20 to 30 mol %. However, the process according to the invention is particularly favorable when the aforementioned propane conversion is from 30 to 60 mol %, preferably from 35 to 55 mol % and more preferably from 35 to 45 mol %.

For the realization of the aforementioned propane conversions, it is favorable to carry out the partial heterogeneously catalyzed propane dehydrogenation in reaction zone A at a working pressure of from 0.3 to 10 bar, or advantageously up to 3 bar. By virtue of the heat capacity of the water, presence of steam enables some of the effects of the endothermicity of the dehydrogenation to be balanced out and the dilution with steam secondly reduces the partial reactant and product pressure, which has a favorable effect on the equilibrium position of the dehydrogenation. Such a diluting action can also be caused by additional use of other inert gases (e.g. $N_2$, $CO_2$, etc.) as further gaseous starting streams. Compared to these, though, steam has, as already stated, additionally an advantageous action on the catalyst lifetime in reaction zone A.

Figure 3:
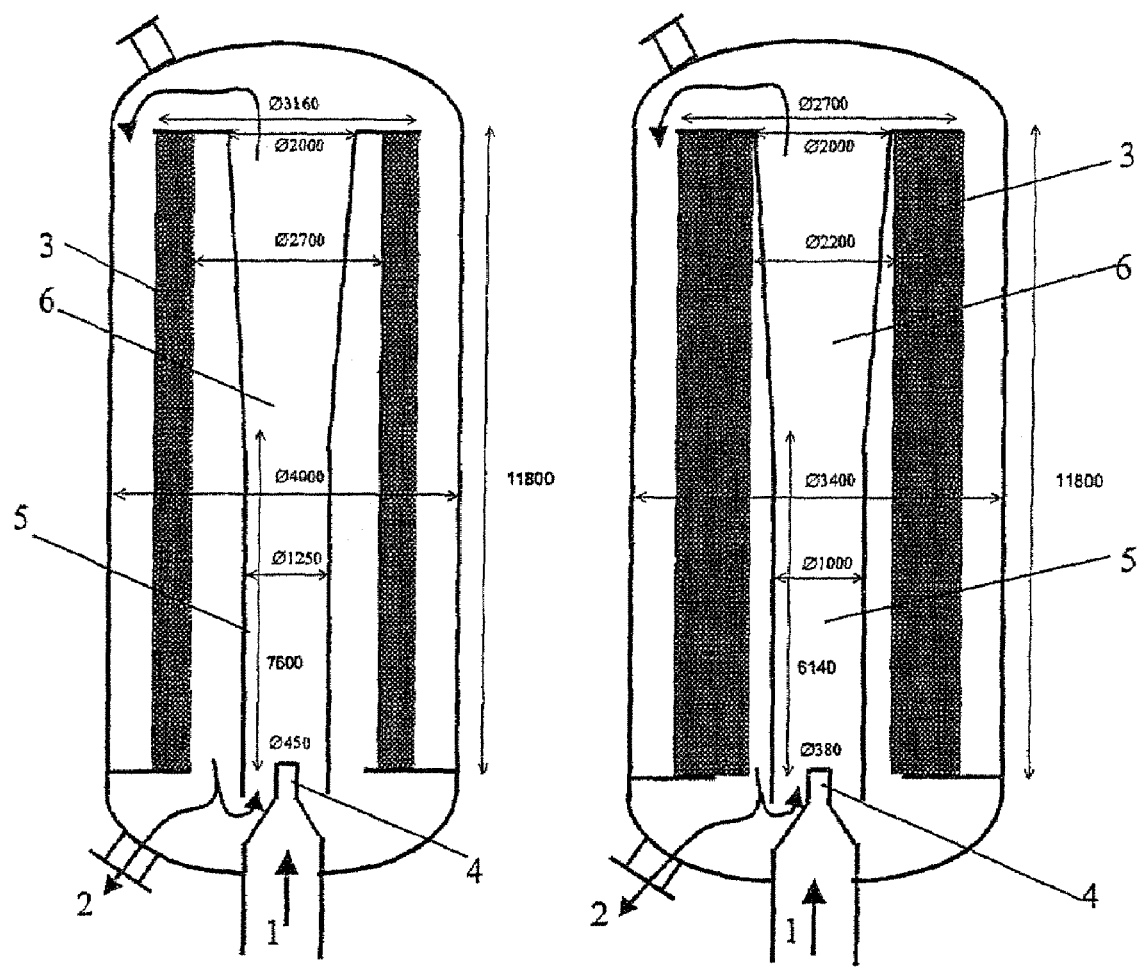

FIG. 3 shows two possible configurations of such a reaction zone A (the diameters specified in FIG. 3 have the dimension "mm"). The numerical addresses mean:
1=motive jet mixture stream
2=product gas mixture A substream 2
3=fixed catalyst bed
4=motive nozzle
5=mixing tube
6=diffuser The motive jet mixture stream may, for example, be 148 t/h, and have a temperature of 486° C. and a pressure of 3.11 bar or of 3.51 bar. In a corresponding manner, product gas mixture A substream 2 is likewise 148 t/h and can, for example, typically have a temperature of 600° C. and a pressure of 2.3 bar. In other words, the pressure on the suction side may be 2.3 bar. This corresponds to a total circulation stream of 296 t/h. The catalyst used may, for example, be extrudates having a diameter of 1.5 mm and a length of typically from 3 to 7 mm in accordance with Example 4 of DE-A 102 19 879 (total amount: for example 30 t). The bulk density thereof in the fixed catalyst bed may, for example, be from 1200 kg/m$^3$ (loose) to 1350 kg/m$^3$ (dense). Immediately upstream of the catalyst bed, a pressure of typically 2.71 bar would then be present.

The significant contents of the reaction gas mixture input stream A are typically:

| | |
|---|---|
| propene | from >0 to 25, in many cases from 1 to 10, frequently from 2 to 7% by volume; |
| scrolein | from 0 to 1, in many cases from 0 to 0.5, frequently from 0 to 0.25% by volume; |
| scrylic acid | from 0 to 0.25, in many cases from 0 to 0.05, frequently from 0 to 0.03% by volume; |
| CO$_x$ | from 0 to 5, in many cases from 0 to 3, frequently from 0 to 2% by volume; |
| propane | from 5 to 50, preferably from 10 to 20% by volume; |
| nitrogen | from 30 to 80, preferably from 50 to 70% by volume; |
| oxygen | from >0 to 5, preferably from 1.0 to 2.0% by volume; |
| H$_2$O | from $\geqq$0 to 20, preferably from 5.0 to 10.0% by volume; |
| H$_2$ | from 0.5 to 10, preferably from 1 to 5% by volume |

However, as already stated, minimum steam contents in reaction gas mixture input stream A are generally preferred and pursued. With increasing propane conversion pursued in reaction zone A, there is a growing requirement for presence of significant amounts of steam in reaction gas mixture input stream A in order to ensure satisfactory lifetimes of the dehydrogenation catalyst.

It is favorable for the process according to the invention when the molar ratio of molecular hydrogen present to molecular oxygen present in reaction gas mixture input stream A is about 2:1. The molar ratio of molecular hydrogen present to propane present in reaction gas mixture input A is generally simultaneously $\leqq$5. The molar ratio of steam present in reaction gas mixture input stream A to propane present therein in the process according to the invention will in many cases be from $\geqq$0.05 to 2 or to 1.

Advantageously, reaction zone A in the process according to the invention is configured such that product gas mixture A comprises unconverted propane and desired propylene in a molar propene to propane ratio of from 0.2 or 0.3 to 0.5 (if appropriate to 0.66).

Based on single pass of reaction gas mixture input stream A through reaction zone A, reaction zone A can be configured isothermally by virtue of controlled heat exchange with (fluid, i.e. liquid or gaseous) heat carriers conducted outside reaction zone A. However, with the same reference basis, it can also be designed adiabatically, i.e. substantially without such a controlled heat exchange with heat carriers conducted outside reaction zone A. In the latter case, the gross thermal character, based on single pass of the reaction gas mixture input stream A fed to reaction zone A through reaction zone A, by taking measures which have been recommended in the documents acknowledged as prior art and are yet to be described below, may be configured endothermically (negative) or autothermally (essentially zero) or exothermically (positive).

Typically, the heterogeneously catalyzed partial dehydrogenation of propane to propylene requires comparatively high reaction temperatures. The achievable conversion is normally restricted by the thermodynamic equilibrium. Typical reaction temperatures are from 300 to 800° C. or from 400 to 700° C. One molecule of hydrogen is obtained per molecule of propane to be dehydrogenated to propylene.

High temperatures and removal of the H$_2$ reaction product shift the equilibrium position toward the target product, as does partial pressure reduction by inert dilution.

In principle, the partial heterogeneously catalyzed propane dehydrogenation in reaction zone A can be carried out (quasi-)adiabatically and at the same time endothermically. In this case, reaction gas mixture input stream A is conducted at a temperature of from 450 to 700° C. (or from 550 to 650° C.) to the at least one catalyst bed. In the course of adiabatic pass through it (both a fluidized bed and a fixed bed are possible; preference is given in accordance with the invention to a fixed catalyst bed), the reaction gas mixture will normally be heated first owing to the hydrogen combustion and then cooled by from 30° C. to 200° C. depending on conversion and dilution. Lower reaction temperatures enable longer lifetimes of the catalyst bed used. Higher reaction temperatures promote increased conversions.

Appropriately from an application point of view, the heterogeneously catalyzed propane dehydrogenation in reaction zone A will be realized in the form of a tray reactor. This appropriately comprises more than one catalyst bed catalyzing the dehydrogenation in spatial succession. The catalyst bed number may be from 1 to 20, appropriately from 2 to 8, but also from 3 to 6. With increasing number of trays, it is increasingly easy to achieve elevated propane conversions. The catalyst beds are preferably arranged in radial or axial succession. Appropriately from an application point of view, the fixed catalyst bed type is employed in such a tray reactor.

In the simplest case, the fixed catalyst beds are arranged axially in a shaft furnace reactor or in the annular gaps of concentric cylindrical grids. However, it is also possible to arrange the annular gaps in segments one above another and to conduct the gas, after it has passed radially through one segment, into the next segment above it or below it.

Appropriately, reaction gas mixture input stream A is subjected to intermediate heating in the tray reactor on its way from one catalyst bed to the next catalyst bed, for example by passing it over heat exchanger surfaces (for example ribs) heated with hot gases or by passing it through pipes heated with hot combustion gases (material appropriately Si-containing steels, especially stainless steels, for example of the 1.4841 type).

When the tray reactor is otherwise operated adiabatically, it is sufficient for propane conversions of $\leqq$30 mol % on the basis as described, in particular when using the catalysts described in DE-A 199 37 107, especially those of the exemplary embodiments, to conduct reaction gas mixture input stream A into the dehydrogenation reactor preheated to a temperature of from 450 to 550° C. and to keep it in this temperature range within the tray reactor. This means that the entire propane dehydrogenation can thus be implemented at extremely low temperatures, which is found to be particularly favorable for the lifetime of the fixed catalyst beds. For higher propane conversions, reaction gas mixture input stream A is appropriately conducted into the dehydrogenation reactor preheated to higher temperatures (these may be up to 700° C.) and kept in this elevated temperature range within the tray reactor.

It is even more elegant to carry out the above-outlined intermediate heating in a direct way (autothermal method). To this end, a limited amount of molecular oxygen is added to the reaction gas mixture stream normally either beyond the first catalyst bed (viewed in flow direction) or between the downstream catalyst beds. It is thus possible (generally catalyzed by the dehydrogenation catalysts themselves) to bring about limited combustion of the molecular hydrogen which is present in the reaction gas mixture, has been formed in the course of the heterogeneously catalyzed propane dehydrogenation and/or has been added to the reaction gas mixture (if appropriate, accompanied to a minor extent by propane combustion) (it may also be appropriate from an application point of view to insert catalyst beds in the tray reactor which are charged with catalysts which particularly specifically (selectively) catalyzes the combustion of hydrogen (useful such catalysts are, for example, those of the documents U.S. Pat. Nos. 4,788,371, 4,886,928, 5,430,209, 5,530,171, 5,527,979 and 5,563,314; for example, such catalyst beds may be accommodated in the tray reactor in alternation to the beds comprising dehydrogenation catalyst). Preferably in accordance with the invention, molecular hydrogen is added from outside only to form reaction gas mixture input stream A. The heat of reaction released thus enables a virtually isothermal operating mode of the heterogeneously catalyzed propane dehydrogenation in a quasi-autothermal manner (the gross thermal character is substantially zero). As the selected residence time of the reaction gas in the catalyst bed is increased, dehydrogenation of propane is thus possible at decreasing or substantially constant temperature, which enables particularly long catalyst lifetimes.

Generally, oxygen feeding as described above should be undertaken such that the oxygen content of the reaction gas mixture, based on the amount of molecular hydrogen present therein, is from 0.5 to 50 or to 30% by volume, preferably from 10 to 25% by volume (these relations are also favorable for the corresponding contents in reaction gas mixture input stream A). Useful oxygen sources are either pure molecular oxygen or oxygen diluted with inert gas, for example CO, $CO_2$, $N_2$ and/or noble gases, dilute oxygen, but in particular also air (preference is given to using exclusively air as the oxygen source). The resulting combustion gases generally additionally have a diluting effect and thus promote the heterogeneously catalyzed propane dehydrogenation. This is especially true of steam formed in the course of combustion.

The isothermicity of the heterogeneously catalyzed propane dehydrogenation can be improved further by incorporating closed (for example tubular) internals which have favorably, but not necessarily, been evacuated before being charged into the spaces between the catalyst beds in the tray reactor. These internals comprise suitable solids or liquids which evaporate or melt above a certain temperature and consume heat as they do so, and, where the temperature falls below this level, condense again and release heat as they do so.

Advantageously, reaction gas mixture input stream A, especially in the case of an autothermal operating mode as described, comprises:

from 15 to 25% by volume of propane,
from 2 to 6% by volume of propylene,
from 5 to 20% by volume of steam,
from 2 to 10% by volume of molecular oxygen,
from 40 to 75% by volume of molecular nitrogen, and
from >0 to 3% by volume of molecular oxygen.

Typical loadings on the entire amount of dehydrogenation catalyst (sum over all beds) with reaction gas mixture input stream A are, in accordance with the invention, from 250 to 5000 $h^{-1}$ (in high-load mode even up to 40 000 $h^{-1}$), preferably from 10 000 to 25 000 l (STP)/l·h, more preferably from 15 000 to 20 000 l (STP) l·h. The corresponding loadings with propane are typically from 50 to 1000 $h^{-1}$ (in high-load mode even up to 40 000 $h^{-1}$), preferably from 2000 to 5000 l (STP)/l·h, more preferably from 3000 to 4000 l (STP)/l·h.

In reaction zone A, the inventive procedure enables propylene formation selectivities of 95 mol% and more even at high propane conversions.

The product gas mixture A-substeam 2 withdrawn from reaction zone A (the dehydrogenation reactor), in accordance with the reaction conditions selected for the heterogeneously catalyzed propane dehydrogenation, is generally at a pressure of from 0.3 to 10 bar, preferably from 1 to 3 bar, and frequently has a temperature of from 450 to 650° C. or to 750° C., in many cases a temperature of from 500 to 600° C. In general, it comprises propane, propene, $H_2$, $N_2$, $H_2O$, methane, ethane (the latter two usually result as a consequence of thermal decomposition of a small amount of propane), ethylene, butene-1, other butenes such as isobutene, other $C_4$ hydrocarbons such as n-butane, isobutane, butadiene, etc., CO and $CO_2$, but generally also oxygenates such as alcohols, aldehydes and carboxylic acids (normally having ≦9 carbon atoms). Small amounts of constituents stemming from gaseous starting steam 2 may also be present.

While EP-A 117 146, DE-A 33 13 573 and U.S. Pat. No. 3,161,670 recommend using product gas mixture A substream 2 to charge the at least one oxidation reactor, it is considered to be advantageous for the process according to the invention to remove at least a portion of the constituents other than propane and propylene present in product gas mixture A substream 2 comprising the required propylene therefrom before it is used as the propene source for the downstream propene partial oxidation. In this case, the requirements of DE-A 102 11 275 should be observed.

It should first be emphasized at this point that all dehydrogenation catalysts known in the prior art are useful in principle for the invention heterogeneously catalyzed propane dehydrogenation. They can be divided roughly into two groups, specifically into those which are of oxidic nature (for example chromium oxide and/or aluminum oxide) and into those which consist of at least one generally comparatively noble metal (for example platinum) deposited on a generally oxidic support. The dehydrogenation catalysts which may be used thus include all of those recommended in WO 01/96 270, EP-A 731 077, DE-A 10211 275, DE-A 10131297, WO 99/46 039, U.S. Pat. No. 4,788,371, EP-A-0 705 136, WO 99/29 420, U.S. Pat. Nos. 4,220,091, 5,430,220, 5,877,369, EP-A-0 117 146, DE-A 199 37 196, DE-A 199 37 105 and DE-A 199 37 107. In particular, the catalyst according to Example 1, Example 2, Example 3 and Example 4 of DE-A 199 37 107 may be used.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the Periodic Table of the Elements, lanthanum and/or tin, with the proviso that the sum of the percentages by weight adds up to 100% by weight.

Also particularly suitable is the dehydrogenation catalyst used in the examples and comparative examples of this document.

Generally, the dehydrogenation catalysts may be catalyst extrudates (diameter typically from 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm). To carry out the heterogeneously catalyzed dehydrogenation in a fluidized bed (or moving bed), more finely divided catalyst will accordingly be used. The fixed catalyst bed in reaction zone A is preferred in accordance with the invention.

In general, the dehydrogenation catalysts (especially those used by way of example in this document and those recommended in DE-A 19937107 (especially the exemplary catalysts of this DE-A)) are such that they are capable of catalyzing both the dehydrogenation of propane and the combustion of propane and of molecular hydrogen. The combustion of hydrogen proceeds very much more rapidly over the catalysts both in comparison to the dehydrogenation of propane and in comparison to its combustion in the case of a competition situation.

In addition, all reactor types and process variants known in the prior art are useful in principle for the heterogeneously catalyzed propane dehydrogenation. Descriptions of such process variants are present, for example, in all prior art documents cited with regard to the dehydrogenation catalysts and the prior art cited at the outset of this document.

A comparatively comprehensive description of dehydrogenation processes suitable in accordance with the invention is also present in Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

Advantageously in accordance with the invention, at least 50% by volume, preferably at least 75% by volume, more preferably at least 90% by volume and most preferably at least 95% by volume of the constituents other than propane and propylene present in product gas mixture A substream 2 will be removed before it is used as the propene source for the partial oxidation of the process according to the invention. In principle, it is possible for this purpose to employ all removal variants described in the documents DE-A 10 2004 032 129, DE-A 10 2005 013 039, DE-A 10 2005 009 891, DE-A 10 2005 010 111, DE-A 10 2005 009 885, DE-A 10 2005 028 798 and DE-A 102 45 585.

A possibility appropriate for the inventive requirements consists, for example, in contacting the preferably cooled (preferably to temperatures of from 10 to 100 or 70° C.) product gas mixture A substream 2, for example at a pressure of from 0.1 to 50 bar, preferably from 5 to 15 bar, and a temperature of, for example, from 0 to 100° C., preferably from 20 to 40° C., with a (preferably high-boiling) organic solvent (preferably a hydrophobic solvent) in which propane and propylene (appropriately preferentially over the other constituents of product gas mixture A substream 2) (for example by simply passing it through). Subsequent desorption, rectification and/or stripping with a gas which behaves inertly with regard to the downstream propylene partial oxidation and/or is required as a reactant in this partial oxidation (for example air or another mixture of molecular oxygen and inert gas) can recover the propane and propylene in a mixture in purified form, and this mixture can be used as the propylene source for the partial oxidation (preference is given to proceeding as described in Comparative Example 1 of the German application DE-A 10 2004 032 129). The offgas of such a absorption, which comprises molecular hydrogen if appropriate, can be subjected, for example, to a pressure swing adsorption and/or membrane separation (for example according to DE-A 10235419) and then the removed hydrogen can be used additionally as a constituent of reaction gas mixture input stream A (as gaseous starting steam 4).

However, the C3 hydrocarbons/C4 hydrocarbons separating factor in the above separating process is comparatively limited and frequently insufficient for the requirements described in DE-A 10245585.

As an alternative to the separation step via absorption described, preference is therefore frequently given for the inventive purposes to a pressure swing adsorption or a pressure rectification.

Suitable absorbents for the above-described absorptive removal are in principle all absorbents which are capable of absorbing propane and propylene. The absorbent is preferably an organic solvent which is preferably hydrophobic and/or high-boiling. Advantageously, this solvent has a boiling point (at a standard pressure of 1 atm) of at least 120° C., preferably of at least 180° C., preferentially of from 200 to 350° C., in particular from 250 to 300° C., more preferably from 260 to 290° C. Appropriately, the flashpoint (at a standard pressure of 1 bar) is above 110° C. Generally suitable as absorbents are relatively nonpolar organic solvents, for example aliphatic hydrocarbons which preferably do not contain any externally active polar group, but also aromatic hydrocarbons. Generally, it is desired that the absorbent has a very high boiling point with simultaneously very high solubility for propane and propylene. Examples of absorbents include aliphatic hydrocarbons, for example $C_8$-$C_{20}$-alkanes or alkenes, or aromatic hydrocarbons, for example middle oil fractions from paraffin distillation or ethers having bulky (sterically demanding) groups on the oxygen atom, or mixtures thereof, to which a polar solvent, for example the dimethyl 1,2-phthalate disclosed in DE-A 43 08 087 may be added. Also suitable are esters of benzoic acid and phthalic acid with straight-chain alkanols containing from 1 to 8 carbon atoms, such as n-butyl benzoate, methyl benzoate, ethyl benzoate, dimethyl phthalate, diethyl phthalate, and also what are known as heat carrier oils such as diphenyl, diphenyl ether and mixtures of diphenyl and diphenyl ether or the chlorine derivatives thereof and triarylalkenes, for example 4-methyl-4'-benzyldiphenylmethane and its isomers, 2-methyl-2'-benzyldiphenylmethane, 2-methyl-4'-benzyldiphenylmethane and 4-methyl-2'-benzyldiphenylmethane, and mixtures of such isomers. A suitable absorbent is a solvent mixture of diphenyl and diphenyl ether, preferably in the azeotropic composition, especially of about 25% by weight of diphenyl (biphenyl) and about 75% by weight of diphenyl ether, for example the Diphyl® obtainable commercially (for example from Bayer Aktiengesellschaft). Frequently, this solvent mixture comprises a solvent such as dimethyl phthalate added in an amount of from 0.1 to 25% by weight based on the entire solvent mixture. Particularly suitable absorbents are also octanes, nonanes, decanes, undecanes, dodecanes, tridecanes, tetradecanes, pentadecanes, hexadecanes, heptadecanes and octadecanes, of which tetradecanes in particular have been found to be particularly suitable. It is favorable when the absorbent used firstly fulfills the abovementioned boiling point but secondly at the same time does not have too high a molecular weight. Advantageously, the molecular weight of the absorbent is $\leq 300$ g/mol. Also suitable are the paraffin oils, described in DE-A 33 13 573, having from 8 to 16 carbon atoms. Examples of suitable commercial products are products sold by Haltermann, such as Halpasols i, such as Halpasol 250/340 i and Halpasol 250/275 i, and also printing ink oils under the names PKWF and Printosol. Preference is given to aromatics-free commercial products, for example those of the PKWFaf type. If they comprise a small residual aromatics content, this may, prior to the use described, advantageously be reduced by rectification and/or adsorption and be lowered to values significantly below 1000 ppm by weight. Further suitable commercial products are n-paraffin ($C_{13}$-$C_{17}$) or Mihagol®5 Erdöl-Raffinerie-Emsland GmbH, LINPAR®14-17 from CONDEA Augusta S.p.A. (Italy) or SASOL Italy S.p.A., normal paraffins (heavy) $C_{14}$-$C_{18}$ from SLOVNAFT in Slovakia.

The contents (reported in area percent of gas chromatography analysis) in the aforementioned products of linear hydrocarbons are typically:

total $C_9$ to $C_{13}$: less than 1%; $C_{14}$: 30 to 40%; $C_{15}$: 20 to 33%; $C_{16}$: 18 to 26%; $C_{17}$: up to 18%; $C_{\geq 18}$: <2%.

A typical composition of the product from SASOL is: $C_{13}$: 0.48%; $C_{14}$: 39.8%; $C_{15}$: 20.8%; $C_{16}$: 18.9%; $C_{17}$: 17.3%; $C_{18}$: 0.91%; $C_{19}$: 0.21%

A typical composition of the product from Haltermann is: $C_{13}$: 0.58%; $C_{14}$: 33.4%; $C_{15}$: 32.8%; $C_{16}$: 25.5%; $C_{17}$: 6.8%; $Cr_{\geq 18}$: <0.2%.

In continuous operation, the composition of the absorbent will change correspondingly as a result of the process.

The performance of the absorption is subject to no particular restrictions. It is possible to use all common processes and conditions known to those skilled in the art. Preference is given to contacting product gas mixture A substream 2 with the absorbent at a pressure of from 1 to 50 bar, preferably from 2 to 20 bar, more preferably from 5 to 15 bar, and a temperature of from 0 to 100° C., in particular from 20 to 50 or 40° C. The absorption may be undertaken either in columns or in quench apparatus. It is possible to work in cocurrent or (preferably) in countercurrent. Suitable absorption columns are, for example, tray columns (having bubble-cap and/or sieve trays), columns having structured packings (for example sheet metal packings having a specific surface area of from 100 to 1000, or to 750 $m^2/m^3$, for example Mellapak® 250 Y) and columns having random packing (for example filled with Raschig packings). However, it is also possible to use trickle and spray towers, graphite block absorbers, surface absorbers such as thick-film and thin-film absorbers, and also plate scrubbers, cross-spray scrubbers and rotary scrubbers. In addition, it may be favorable to allow the absorption to take place in a bubble column with and without internals.

The propane and the propylene may be removed from the absorbent by stripping, flash evaporation (flashing) and/or distillation.

The propane and propylene are preferably removed from the absorbent by stripping and/or desorption. The desorption may be carried out in a customary manner by a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 30 to 50° C. An example of a gas suitable for the stripping is steam, but preference is given in particular to oxygen/nitrogen mixtures, for example air. When air or oxygen/nitrogen mixtures are used in which the oxygen content is above 10% by volume, it may be sensible to add a gas before and/or during the stripping process which reduces the explosion range. Particularly suitable for this purpose are gases having a specific heat capacity of $\geq 29$ J/mol·K at 20° C., for example methane, ethane, propane (preferred), propene, benzene, methanol, ethanol, and ammonia, carbon dioxide and water. However, preference is given in accordance with the invention to avoiding C4 hydrocarbons as such additives. Particularly suitable for the stripping are also bubble columns with and without internals.

The propane and propylene may also be removed from the absorbent by a distillation or rectification, in which case the columns which are familiar to those skilled in the art and have structured packings, random packings or appropriate internals can be used. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used to change the partial oxidation, a propylene source which is suitable in principle for reaction zone B of the process according to the invention and has been obtained from the absorbent by stripping may be fed to a further process stage, in order, for example, to reduce the losses of entrained absorbent (for example separation in demisters and/or depth filters) and to thus simultaneously protect the partial oxidation to be carried out in accordance with the invention from absorbent or in order to further improve the separating action between C3/C4 hydrocarbons. Such a removal of the absorbent may be effected by all process steps known to those skilled in the art. An example of an embodiment of such a removal preferred in the process according to the invention is the quenching of the outlet stream from the stripping apparatus with water. In this case, the absorbent is washed out of this laden outlet stream with water and the outlet stream is simultaneously laden with water (small amounts of water have a promoting effect on the activity of the catalysts for the inventive partial oxidation). This scrubbing or the quenching may be effected, for example, at the top of a desorption column using a liquid collecting tray by counterspraying of water or in a dedicated apparatus.

To support the separating effect, it is possible to install internals which increase the quench surface area in the quench chamber, as are known to those skilled in the art from rectifications, absorptions and desorptions.

Water is a preferred scrubbing agent in that it normally does not interfere in the downstream partial oxidation. After the water has washed the absorbent out of the outlet stream laden with propane and propylene, the water/absorbent mixture may be fed to a phase separation and the treated, low-volume outlet stream fed directly to partial oxidation to be carried out in accordance with the invention.

In a manner advantageous for the process according to the invention, especially when the propylene/propane mixture is stripped by means of air to free it of the absorbate, starting reaction gas mixtures usable for the partial oxidation can generally be obtained directly. In the case that their propane content should not yet be satisfactory in accordance with the invention, it is possible also to add fresh propane to them before they are used for the partial oxidation of the propylene present to be carried out in accordance with the invention. Via the residual gas (gaseous starting steam 2), fresh propane is then appropriately recycled into the heterogeneously catalyzed dehydrogenation (as a constituent of reaction gas mixture input stream A). The supply of fresh propane via the gaseous starting gas stream 3 can then be reduced by the appropriate amount of propane. In the extreme case, the supply of fresh propane required in the heterogeneously catalyzed propane dehydrogenation can be dispensed with entirely when this fresh propane, before the partial oxidation of propylene is carried out, is supplied fully into this starting reaction gas mixture, whence it is then fed as a remaining constituent in the residual gas, only after passing through the partial oxidation to be carried out in accordance with the invention, to reaction gas mixture input stream A for the heterogeneously catalyzed propane dehydrogenation. If appropriate, fresh propane may also be supplied into any $C_3$ removal (for example as stripping gas) disposed between heterogeneously catalyzed dehydrogenation and propylene partial oxidation.

When the reaction is a two-stage partial oxidation of propylene to acrylic acid, some or even all of the fresh propane may also be supplied into the starting reaction gas mixture for the second stage of the partial oxidation (however, this starting reaction gas mixture is sometimes not explosive even when this qualification was actually true for the starting reaction gas mixture for the first stage of the partial oxidation). This is advantageous in particular because the undesired side reaction of propane to give propionaldehyde and/or propionic acid starts in particular from the first partial oxidation stage (propylene→acrolein) under the conditions thereof. It is also advantageous to divide a fresh propane supply substantially uniformly between the first and the second partial oxidation stage.

As a result of this possibility of supplying fresh propane into the starting reaction gas mixture for the partial oxidation stages, the composition of these starting reaction gas mixtures can reliably be made nonexplosive. If appropriate, a portion of residual gas can also be recycled directly into the propylene and/or acrolein partial oxidation for this purpose. If required, it is also possible to use a mixture of fresh propane and residual gas for this purpose. A crucial factor in answering the question of whether the starting reaction gas mixture for a partial oxidation stage is explosive or not is whether combustion (ignition, explosion) initiated by a local ignition source (for example glowing platinum wire) spreads in the starting reaction gas mixture under certain starting conditions (pressure, temperature) or not (cf. DIN 51649 and the experiment description in WO 04/007405). When there is spreading, the mixture shall be referred to here as explosive. When there is no spreading, the mixture is classified as nonexplosive in this document. When the starting reaction gas mixture is nonexplosive, this also applies to the reaction gas mixtures formed in the course of the inventive partial oxidation of propylene (cf. WO 04/007 405).

In general, however, only reaction gas mixture input stream A will comprise added fresh propane in the process according to the invention.

The present invention also relates to process configurations in which the fresh propane required for the process is supplied at most partly (for example only to an extent of 75%, or only to extent of 50%, or only to an extent of 25%) to reaction gas mixture input stream A and at least partly (generally the remainder, if appropriate the entirety) to the reaction gas mixture starting gas(es) of the partial oxidation. Otherwise, the procedure may be as described in WO 01/96 170, which forms an integral part of this application.

In a manner known per se, the heterogeneously catalyzed gas phase partial oxidation of propylene to acrylic acid with molecular oxygen proceeds in principle in two steps successive along the reaction coordinate, of which the first leads to acrolein, and the second from acrolein to acrylic acid.

This reaction sequence in two steps successive in time opens up the possibility in a manner known per se of terminating the process according to the invention at the stage of acrolein (the stage of predominant acrolein formation) and undertaking the target product removal at this stage, or continuing the process according to the invention up to predominant acrylic acid formation and only then undertaking the target product removal.

When the process according to the invention is carried out up to predominant acrylic acid formation, it is advantageous in accordance with the invention to perform the process in two stages, i.e. in two oxidation stages arranged in series, in which case the fixed catalyst bed to be used and preferably also the other reaction conditions, for example the temperature of the fixed catalyst bed, are appropriately adjusted in an optimizing manner in each of the two oxidation stages.

Although the multimetal oxides comprising the elements Mo, Fe, Bi which are particularly suitable as active compositions for the catalysts of the first oxidation stage (propylene→acrolein) are also capable to a certain extent of catalyzing the second oxidation stage (acrolein→acrylic acid), preference is normally given for the second oxidation stage to catalysts whose active composition is at least one multimetal oxide comprising the elements Mo and V.

The process according to the invention for the heterogeneously catalyzed partial oxidation of propylene over fixed catalyst beds whose catalysts have, as an active composition, at least one multimetal oxide comprising the elements Mo, Fe and Bi is thus suitable in particular as a one-stage process for preparing acrolein (and acrylic acid if appropriate) or as the first reaction stage for the two-stage preparation of acrylic acid.

The realization of the one-stage heterogeneously catalyzed partial oxidation of propylene to acrolein and acrylic acid if appropriate or the two-stage heterogeneously catalyzed partial oxidation of propylene to acrylic acid using an inventive starting reaction gas mixture may specifically be carried out as described in the documents EP-A 700 714 (first reaction stage; as described there, but also in corresponding countercurrent mode of salt bath and starting reaction gas mixture over the tube bundle reactor), EP-A 700 893 (second reaction stage; as described there, but also in corresponding countercurrent mode), WO 04/085 369 (especially this document is considered to be an integral part of this document) (as a two-stage process), WO 04/85 363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (one-stage or two-stage), WO 04/085 368 (as a two-stage process), DE-A 10 2004 021 764 (two-stage), WO 04/085 362 (first reaction stage), WO 04/085 370 (second reaction stage), WO 04/085 365 (second reaction stage), WO 04/085 367 (two-stage), EP-A 990 636, EP-A 1 007 007 and EP-A 1 106 598.

This is especially true of all working examples contained in these documents. They may be carried out as described in these documents, but with the difference that the starting reaction gas mixture used for the first reaction stage (propylene to acrolein) is an inventive starting reaction gas mixture 2. Regarding the remaining parameters, the procedure is as in the working examples of the documents mentioned (especially regarding the fixed catalyst beds and reactant loading on the fixed catalyst beds). When the procedure in the aforementioned working examples of the prior art is in two stages and there is secondary oxygen (secondary air) feeding between the two reaction stages, the feeding is undertaken in an appropriate manner, but is adjusted in its amount to the effect that the molar ratio of molecular oxygen to acrolein in the charge mixture of the second reaction stage corresponds to that in the working examples of the documents mentioned. An inventive starting reaction gas mixture for the heterogeneously catalyzed partial gas phase oxidation is obtainable in a simple manner, for example, by adding as much molecular oxygen to product gas mixture A substream 2 or to product gas mixture stream A' as is required for the partial oxidation. This supply can be effected in the form of pure molecular oxygen or else in the form of a mixture of molecular oxygen and of inert gas (or else only in the presence of inert gas). Preference is given in accordance with the invention to air as such a mixture. It is essential to the invention that this oxygen supply is effected in such a way that product gas mixture B still comprises unconverted molecular oxygen.

In general, the molar ratio of molecular oxygen present in the starting reaction gas mixture for the partial oxidation to propylene present in the starting reaction gas mixture for the partial oxidation is ≧1 and ≦3.

Multimetal oxide catalysts particularly suitable for the particular reaction stage have been described many times before and are well known to those skilled in the art. For example, EP-A 253 409 refers on page 5 to corresponding US patents.

Favorable catalysts for the particular oxidation stage are also disclosed by DE-A 4 431 957, DE-A 10 2004 025 445 and DE-A 4 431 949. This is especially true of those of the general formula I in the two aforementioned documents. Particularly advantageous catalysts for the particular oxidation stage are disclosed by the documents DE-A 103 25 488, DE-A 103 25 487, DE-A 103 53 954, DE-A 103 44 149, DE-A 103 51 269, DE-A 103 50 812, DE-A 103 50 822.

For the inventive reaction stage for the heterogeneously catalyzed gas phase partial oxidation of propylene to acrolein or acrylic acid or a mixture thereof, useful multimetal oxide compositions are in principle all multimetal oxide compositions comprising Mo, Bi and Fe as the active composition.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 700 714.

Also suitable for this reaction stage are the multimetal oxide catalysts comprising Mo, Bi and Fe which are disclosed in the documents Research Disclosure No. 497012 of Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 279 374, DE-A 330 00 44, EP-A 575 897, U.S. Pat. No. 4,438,217, DE-A 19855913, WO 98/24 746, DE-A 197 46 210 (those of the general formula II), JP-A 91/294 239, EP-A 293 224 and EP-A 700 714. This applies in particular to the exemplary embodiments in these documents, and among these particular preference is given to those of EP-A 15 565, EP-A 575 897, DE-A 197 46 210 and DE-A 198 55 913. Particular emphasis is given in this context to a catalyst according to Example 1 c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10\ SiO_2$. Emphasis is also given to the example having the serial number 3 from DE-A 198 55 913 (stoichiometry:

$Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to Example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein and, if appropriate, acrylic acid can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. They may of course also be used as catalysts in powder form.

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the "propylene→acrolein (and acrylic acid if appropriate)" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 2 909 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions to be used for the step from propylene to acrolein are also compositions of the general formula V

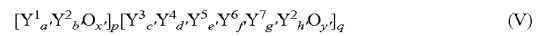

$$[Y^1{}_{a'}Y^2{}_{b'}O_{x'}]_p[Y^3{}_{c'}Y^4{}_{d'}Y^5{}_{e'}Y^6{}_{f'}Y^7{}_{g'}Y^2{}_{h'}O_{y'}]_q \qquad (V)$$

in which the variables are each defined as follows:
$Y^1$=only bismuth or bismuth and at least one of the elements tellurium, antimony, tin and copper,
$Y^2$=molybdenum or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10, comprising three-dimensional regions of the chemical composition $Y^1{}_{a'}Y^2{}_{b'}O_{x'}$ which are delimited from their local environment owing to their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions V in accordance with the invention are those in which $Y^1$ is only bismuth.

Among these, preference is given in turn to those of the general formula VI

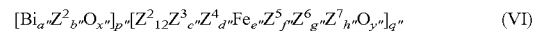

$$[Bi_{a''}Z^2{}_{b''}O_{x''}]_{p''}[Z^2{}_{12}Z^3{}_{c''}Z^4{}_{d''}Fe_{e''}Z^5{}_{f''}Z^6{}_{g''}Z^7{}_{h''}O_{y''}]_{q''} \qquad (VI)$$

in which the variables are each defined as follows:
$Z^2$=molybdenum or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3, f″=from 0 to 5,
g″=from 0 to 10,
h″=from 0 to 1,
x″,y″=numbers which are determined by the valency and frequency of the elements in VI other than oxygen,
p″,q″=numbers whose p″/q″ ratio is from 0.1 to 5, preferably from 0.5 to 2, and very particular preference is given to those compositions VI in which $Z^2_{b''}=$(tungsten)$_{b''}$ and $Z^2_{12}=$(molybdenum)$_{12}$.

It is also advantageous when at least 25 mol % (preferably at least 50 mol % and more preferably at least 100 mol %) of the total proportion of $[Y^1_a Y^2_b O_x]_p$ ($[Bi_{a''} Z^2_{b''} O_{x''}]_{p''}$) multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_{a''} Y^2_b O_x [Bi_{a''} Z^2_{b''} O_{x''}]$ which are delimited from their local environment owing to their different chemical composition from their local environment, and whose maximum diameter is in the range from 1 nm to 100 μm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

For the second step (the second reaction stage), the heterogeneously catalyzed gas phase partial oxidation of acrolein to acrylic acid, useful active compositions for the catalysts required are, as already stated, in principle all multimetal oxide compositions comprising Mo and V, for example those of DE-A 100 46 928.

A multitude thereof, for example those of DE-A 198 15 281, can be encompassed by the general formula VII

    (VII)

in which the variables are each defined as follows:
X¹=W, Nb, Ta, Cr and/or Ce,
X²=Cu, Ni, Co, Fe, Mn and/or Zn,
X³=Sb and/or Bi,
X⁴=one or more alkali metals,
X⁵=one or more alkaline earth metals,
X⁶=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VIII:
X¹=W, Nb and/or Cr,
X²=Cu, Ni, Co and/or Fe,
X³=Sb,
X⁴=Na and/or K,
X⁵=Ca, Sr and/or Ba,
X⁶=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly preferred in accordance with the invention are those of the general formula VIII

    (VIII)

where
Y¹=W and/or Nb,
Y²=Cu and/or Ni,
Y⁵=Ca and/or Sr,
Y⁶=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as H₂, NH₃, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). The fineness of the catalytically active oxide compositions to be applied to the surface of the support body is of course adapted to the desired coating thickness (cf. EP-A 714 700).

Favorable multimetal oxide active compositions to be used for the "acrolein→acrylic acid" step are also compositions of the general formula IX $$[D]_p[E]_q \quad (IX)$$

in which the variables are each defined as follows:
$D=Mo_{12}V_{a''}Z^1_{b''}Z^2_{c''}Z^3_{d''}Z^4_{e''}Z^5_{f''}Z^6_{g''}O_{x''}$,
$E=Z^7_{12}Cu_{h''}H_{i''}O_{y''}$, $Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements in IX other than oxygen and
p,q=numbers other than zero whose p/q ratio is from 160:1 to 1:1, and which are obtainable by separately preforming a multimetal oxide composition E $$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the above-mentioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 198 15 281, especially having multimetal oxide active compositions of the general formula I of this document.

Advantageously, unsupported catalyst rings are used for the step from propylene to acrolein and coated catalyst rings for the step from acrolein to acrylic acid.

The performance of the partial oxidation of the process according to the invention, from propylene to acrolein (and acrylic acid if appropriate), may be carried out with the catalysts described, for example, in a single-zone multiple catalyst tube fixed bed reactor, as described by DE-A 4 431 957. In this case, reaction gas mixture and heat carrier (heat exchange medium) may be conducted in cocurrent or in countercurrent viewed over the reactor.

The reaction pressure is typically in the range from 1 to 3 bar and the overall space velocity on the fixed catalyst bed of (starting) reaction gas mixture 2 is preferably from 1500 to 4000 or 6000 l (STP)/l·h or more. The propylene loading (the propylene hourly space velocity on the fixed catalyst bed) is typically from 90 to 200 l (STP)/l·h or to 300 l (STP)/l·h or more. Propylene loadings above 135 l (STP)/l·h or ≧140 l (STP)/l·h, or ≧150 l (STP)/l·h, or ≧160 l (STP)/l·h are particularly preferred in accordance with the invention, since the inventive starting reaction gas mixture, owing to the presence of unconverted propane, causes favorable hotspot behavior (all of the aforementioned applies irrespective of the specific selection of the fixed bed reactor).

The flow to the single-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture may, as already stated, be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 30 or up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Research Disclosure No. 497012 of Aug. 29, 2005, or according to Example 1 of DE-A 100 46 957 or according to Example 3 of DE-A 100 46 957 and the inert material used is steatite rings having the geometry 7 mm×7 mm×4 mm (external diameter×height×internal diameter). With regard to the salt bath temperature, the statements of DE-A 4 431 957 apply.

However, the performance of the inventive partial oxidation, from propylene to acrolein (and acrylic acid if appropriate), may also be carried out with the catalysts described, for example, in a two-zone multiple catalyst tube fixed bed reactor, as described by DE-A 199 10 506, DE-A 10 2005 009 885, DE-A 10 2004 032 129, DE-A 10 2005 013 039 and DE-A 10 2005 009 891, and also DE-A 10 2005 010 111. In both of the above-described cases (and quite generally in the process according to the invention), the propene conversion achieved in single pass is normally at values of 24 90 mol %, or ≧95 mol %, and the selectivity of acrolein formation at values of ≧90 mol %. Advantageously in accordance with the invention, the inventive partial oxidation of propene to acrolein, or acrylic acid or mixtures thereof, is effected as described in EP-A 1 159 244 und most preferably as described in WO 04/085 363 and in WO 04/085 362.

The documents EP-A 1 159 244, WO 04/085 363 and WO 04/085 362 are considered to be an integral part of this document.

In other words, the inventive partial oxidation of propylene can be carried out particularly advantageously over a fixed catalyst bed having increased propylene hourly space velocity and at least two temperature zones.

In this regard, reference is made, for example, to EP-A 1 159 244 and WO 04/085 362.

A typical composition of the starting reaction gas mixture for the partial oxidation of propylene to acrolein may, in the process according to the invention, comprise:

from 5 to 9% by volume of propylene,
from 8 to 18% by volume of molecular oxygen,
from 6 to 30 (or to 35)% by volume of propane and
from 32 to 72% by volume of molecular nitrogen.

The performance of the second step in the case of a two-stage partial oxidation of propylene to acrolein, i.e. the partial oxidation of acrolein to acrylic acid, may be carried out with the catalysts described, for example, in a one-zone multiple catalyst tube fixed bed reactor as described in DE-A 44 31 949. In this reaction stage, reaction gas mixture and heat carrier can be conducted in cocurrent viewed over the reactor. In general, the product gas mixture of the preceding inventive propylene partial oxidation to acrolein is in principle conducted as such (if appropriate after intermediate cooling (this may be effected indirectly or directly by, for example, secondary air addition) thereof), i.e. without secondary component removal, into the second reaction stage, i.e. into the acrolein partial oxidation.

The molecular oxygen required for the second step, the acrolein partial oxidation, may already be present in the starting reaction gas mixture for the inventive propylene partial oxidation to acrolein. However, it may also be added partly or fully directly to the product gas mixture of the first reaction stage, i.e. the inventive propylene partial oxidation to acrolein (this is preferably effected in the form of (secondary) air, but may also be effected in the form of pure oxygen or of mixtures of inert gas or oxygen). Irrespective of the procedure, the charge gas mixture (starting reaction gas mixture) of such a partial oxidation of acrolein to acrylic acid advantageously has the following contents:

| | |
|---|---|
| from 4 to 8% by volume of | acrolein, |
| from 2.25 or 4.5 to 9% by volume of | molecular oxygen, |
| from 6 to 30% by volume of | propane, |
| from 32 to 72% by volume of | molecular nitrogen, |
| from 5 to 15% by volume of | steam. |

The aforementioned starting reaction gas mixture preferably has the following contents:

| | |
|---|---|
| from 5 to 8% by volume of | acrolein, |
| from 2.75 or 5.5 to 9% by volume of | molecular oxygen, |
| from 10 to 25% by volume of | propane, |
| from 40 to 70% by volume of | molecular nitrogen, |
| from 5 to 15% by volume of | steam. |

The aforementioned starting reaction gas mixture most preferably has the following contents:

| | |
|---|---|
| from 5 to 8% by volume of | acrolein (preferably from 6 to 7% by volume) |
| from 3 or 6 to 9% by volume of | molecular oxygen, |
| from 10 to 20% by volume of | propane (preferably from 10 to 16% by volume) |
| from 50 to 65% by volume of | molecular nitrogen, |
| from 7 to 13% by volume of | steam, | the preferred ranges applying independently of one another, but advantageously being realized simultaneously.

As in the first reaction stage (propylene→acrolein), the reaction pressure in the second reaction stage (acrolein→acrylic acid) too is typically in the range from 1 to 3 bar and the total space velocity on the fixed catalyst bed of (starting) reaction gas mixture is preferably from 1500 to 4000 or 6000 l (STP)/l·h or more. The acrolein loading (the acrolein hourly space velocity on the fixed catalyst bed) is typically from 90 to 190 l (STP)/l·h, or to 290 l (STP)/l·h or more. Acrolein loadings above 135 l (STP)/l·h, or ≧140 l (STP)/l·h, or ≧150 l (STP)/l·h, or ≧160 l (STP)/l·h are particularly preferred, since the starting reaction gas mixture to be used in accordance with the invention likewise causes favorable hotspot behavior.

The acrolein conversion based on single pass of starting reaction gas mixture through the fixed catalyst bed is appropriately normally ≧90 mol % and the accompanying selectivity of acrylic acid formation ≧90 mol %.

The flow to the single-zone multiple catalyst tube fixed bed reactor of the charge gas mixture is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows:

first, to a length of from 50 to 80 or to 70% of the catalyst tube length, either only catalyst or a mixture of catalyst and inert material, the latter, based on the mixture, making up a proportion by weight of up to 30 (or up to 20) % by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on the fixed catalyst bed and high steam contents of the charge gas mixture), section B may also consist of two successive catalyst dilutions (for the purpose of minimizing hotspot temperature and hotspot temperature sensitivity). From bottom to top, first with up to 30 (or 20)% by weight of inert material and subsequently with from >20% by weight to 50 or to 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to preparation example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion achieved in single pass is normally ≧90 mol %, or ≧95 mol % or ≧99 mol %.

However, the performance of the partial oxidation of acrolein to acrylic acid may also be carried out with the catalysts described, for example, in a two-zone multiple catalyst tube fixed bed reactor as described in DE-199 10 508. For the acrolein conversion, the above statements apply. Also in the case in which an acrolein partial oxidation as described above is carried out as the second stage of a two-stage propylene oxidation to acrylic acid in a two-zone multiple catalyst tube fixed bed reactor, the charge gas mixture (starting reaction gas mixture) will appropriately be obtained directly by using the product gas mixture of the partial oxidation directed to the first step (if appropriate after indirect or direct (for example by supplying secondary air) intermediate cooling thereof) (as has already been described above). The oxygen required for the acrolein partial oxidation is preferably added in the form of air (if appropriate also in the form of pure molecular oxygen or in the form of a mixture of molecular oxygen and an inert gas) and, for example, added directly to the product gas mixture of the first step of the two-stage partial oxidation (propylene→acrolein). However, it may also, as already described, already be present in the starting reaction gas mixture for the first reaction stage.

In a two-stage partial oxidation of propylene to acrylic acid with direct further use of the product gas mixture of the first step of the partial oxidation to charge the second step of the partial oxidation, two one-zone multiple catalyst tube fixed bed reactors (at high reactant hourly space velocity on the catalyst bed, as is quite generally the case, preference is given to countercurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Between the reactors may be disposed an intermediate cooler which may if appropriate comprise inert beds which can perform a filter function. The salt bath temperature of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input and their output temperature is generally ≧5° C. As already mentioned, both steps of the partial oxidation of propylene to acrylic acid may also be implemented in one reactor over one charge, as described in DE-A 101 21 592.

It should also be mentioned once again that a portion of the starting reaction gas mixture for the first step ("propylene→acrolein") may be residual gas coming from the partial oxidation.

This is, as already stated, a gas which comprises molecular oxygen and remains after the target product removal (acrolein and/or acrylic acid removal) from the product gas mixture of the partial oxidation and may be recycled partly as inert diluent gas into the charge for the first and/or if appropriate second step of the partial oxidation of propylene to acrolein and/or acrylic acid.

However, such residual gas comprising propane, molecular oxygen and any unconverted propylene will preferably, advantageously in accordance with the invention, be recycled exclusively as gaseous starting stream 2 into the heterogeneously catalyzed propane dehydrogenation in reaction zone A.

Overall, a tube bundle reactor within which the catalyst charge changes appropriately along the individual catalyst tubes with completion of the first reaction step (such two-stage propylene partial oxidations in a single reactor are taught, for example, by EP-A 911 313, EP-A 979 813, EP-A 990 636 and DE-A 28 30 765) forms the simplest implementation form of the two oxidation stages for the two steps of the partial oxidation from propylene to acrylic acid. If appropriate, the charge of the catalyst tubes with catalyst is interrupted by an inert material bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture which leaves the first oxidation zone. The reaction temperature in the first reaction stage (propylene→acrolein) is generally from 300 to 450° C., preferably from 320 to 390° C. The reaction temperature in the second reaction stage (acrolein acrylic acid) is generally from 200 to 370° C., frequently from 220 to 330° C. The reaction pressure in both oxidation zones is appropriately from 0.5 to 5 bar, advantageously from 1 to 3 bar. The hourly space velocity (l (STP)/l·h) on the oxidation catalysts of reaction gas in both reaction stages is frequently from 1500 to 2500 l (STP)/l·h or to 4000 l (STP)/l·h. The hourly space velocity of propylene may be from 100 to 200 or 300 and more l (STP)/l·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry has an advantageous effect on the kinetics of the particular gas phase partial oxidation and on the catalyst lifetime.

In principle, it is also possible to realize the heterogeneously catalyzed gas phase partial oxidation of propylene to acrylic acid to be carried out in accordance with the invention in a single tube bundle reactor as follows. Both reaction steps proceed in an oxidation reactor which is charged with one or more catalysts whose active composition is a multimetal oxide which comprises the elements Mo, Fe and Bi and is capable of catalyzing the reaction of both reaction steps. This catalyst charge can of course change continuously or abruptly along the reaction coordinate. Of course, it is possible in one embodiment of an inventive two-stage partial oxidation of propylene to acrylic acid in the form of two oxidation stages connected in series to partly or fully remove carbon dioxide and steam which have formed as a by-product in the first oxidation stage and are present in the product gas mixture leaving the first oxidation stage from this product gas mixture, if required, before it is passed on into the second oxidation stage. Preference is given in accordance with the invention to selecting a procedure which does not provide for such a removal.

Useful sources for intermediate oxygen feeding carried out between the two oxidation stages are, as already stated, in addition to air (preferred), either pure molecular oxygen or molecular oxygen diluted with inert gas such as $CO_2$, CO, noble gases, $N_2$ and/or saturated hydrocarbons.

In the process according to the invention, metering of, for example, cold air to the product gas mixture of the first partial oxidation stage can also bring about cooling thereof by a direct route before it is used further as a constituent of a starting reaction gas mixture for the second partial oxidation stage.

Advantageously in accordance with the invention, the partial oxidation of acrolein to acrylic acid is effected as described in EP-A 1 159 246 and most preferably as described in WO 04/085 365 and in WO 04/085 370. However, preference is given in accordance with the invention to using, as the starting reaction gas mixture comprising acrolein, a starting reaction gas mixture which is the product gas mixture of an inventive first-stage partial oxidation of propylene to acrolein, which has if appropriate been supplemented with sufficient secondary air that the ratio of molecular oxygen to acrolein in the resulting starting reaction gas mixture is in each case from 0.5 to 1.5. The documents EP-A 1 159 246, WO 04/08 536 and WO 04/085 370 are considered to be an integral part of this document.

In other words, the inventive partial oxidation of acrolein to acrylic acid can be carried out with increased acrolein hourly space velocity advantageously over a fixed catalyst bed which has at least two temperature zones.

Overall, a two-stage partial oxidation of propylene to acrylic acid will preferably be carried out as described in EP-A 1 159 248 or in WO 04/085 367 or WO 04/085 369.

The product gas mixture stream B which leaves the partial oxidation to be carried out in accordance with the invention (after the first and/or the second reaction stage) is, in the case of a preparation of acrolein and/or acrylic acid, composed substantially of the target product acrolein or acrylic acid or a mixture thereof with acrolein, unconverted molecular oxygen (with a view to the lifetime of the catalysts used, it is favorable when the oxygen content in the product gas mixture of both partial oxidation stages is still from at least 1.5 to 4% by volume), propane, unconverted propylene, molecular nitrogen, steam which has formed as a by-product and/or has been used as a diluent gas, carbon oxides which have been formed as a by-product and/or used as a diluent gas, and small amounts of other lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid), in some cases further hydrocarbons, for example C4 hydrocarbons (e.g. butene-1 and possible other butenes), and other inert diluent gases.

The target product may be removed from product gas mixture B in a manner known per se in a separating zone B (for example by partial or full and, if appropriate, fractional condensation of acrylic acid, or by absorption of acrylic acid in water or in a high-boiling hydrophobic organic solvent, or by absorption of acrolein in water or in aqueous solutions of lower carboxylic acids and subsequent workup of the condensates and/or absorbates; according to the invention, product gas mixture B will preferably be fractionally condensed; cf., for example, EP-A 1 388 533, EP-A 1 388 532, DE-A 102 35 847, EP-A 7 92 867, WO 98/01 415, EP-A 1 015 411, EP-A 1 015 410, WO 99/50 219, WO 00/53 560, WO 02/09 839, DE-A 102 35 847, WO 03/041 833, DE-A 102 23 058, DE-A 102 43 625, DE-A 103 36 386, EP-A 854 129, U.S. Pat. No. 4,317,926, DE-A 198 37 520, DE-A 196 06 877, DE-A 190 50 1325, DE-A 102 47 240, DE-A 197 40 253, EP-A 695 736, EP-A 982 287, EP-A 1 041 062, EP-A 1 17 146, DE-A 43 08 087, DE-A 43 35 172, DE-A 44 36 243, DE-A 199 24 532, DE-A 103 32 758 and DE-A 199 24 533). An acrylic acid removal may also be undertaken as in EP-A 982 287, EP-A 982 289, DE-A 103 36 386, DE-A 101 15 277, DE-A 196 06 877, DE-A 197 40 252, DE-A 196 27 847, EP-A 920 408, EP-A 1 068 174, EP-A 1 066 239, EP-A 1 066 240, WO 00/53 560, WO 00/53 561, DE-A 100 53 086 and EP-A 982 288. Preference is given to removing as described in FIG. 7 of WO/0 196 271 or as described in DE-A 10 2004 032 129 and its equivalent patents. Favorable removal methods are also the processes described in the documents WO 04/063 138, WO 04/035 514, DE-A 102 43 625 and DE-A 102 35 847. Crude acrylic acid obtained in this way may be further processed, for example, as described in the documents WO 01/77 056, WO 03/041 832, WO 02/055 469, WO 03/078 378 and WO 03/041 833.

A common feature of the above separating processes is (as already mentioned at the outset) that a residual gas stream which comprises substantially those constituents of product gas mixture B whose boiling point at standard pressure (1 bar) is $\leq -30°$ C. (i.e. the constituents which are difficult to condense or else volatile) normally remains at the top of the particular separating column which comprises separating internals and in whose lower section product gas mixture B is fed, normally after preceding direct and/or indirect cooling thereof.

In the lower section of the separating column, the less volatile constituents of product gas mixture B, including the particular target product, are normally obtained in the condensed phase.

The residual gas constituents are primarily propane, any propylene which has not been converted in the partial oxidation, molecular oxygen and other inert diluent gases which are frequently also used in the partial oxidation, for example nitrogen and carbon dioxide. Depending on the separation process employed, steam may be present in the residual gas only in traces or in amounts of up to 20% by volume or more.

According to the invention, at least a portion (preferably the entire amount, if appropriate however only half, or two thirds, or three quarters, of this entire amount), (preferably having residual gas composition) comprising propane, molecular oxygen and any unconverted propylene, of this main residual gas is recycled as the gaseous starting stream 2 into reaction zone A. However, portions of residual gas may also be recycled into one or into both stages of the partial oxidation and/or be incinerated for the purpose of energy generation.

Of course, it is also possible, as described in this document and in EP-A 1 17 146, U.S. Pat. No. 3,161,670, DE-A 33 13 573 and DE-A 103 16 039, prior to use of residual gas as gaseous starting stream 2, to partly or fully remove especially constituents other than propane, propylene and molecular oxygen from the residual gas.

In the workup of the condensed phase (for the purpose of removing the target product), further residual gases may occur, since it will normally be attempted to recycle the total amount of unconverted propane present in product gas mixture B into reaction zone A and to recover it in the target removal. Although they generally still comprise propane and in some cases propylene, they frequently no longer comprise any molecular oxygen. Typically, they are recycled, combined with the main residual gas to give an overall residual gas, as the gaseous starting stream 2 into reaction zone A. However, it is also possible to separately utilize such further residual gases or to recycle them into reaction zone A.

The preferably full recycling of the remaining overall residual gas thus allows continuous conversion of propane to acrylic acid and/or acrolein in continuous operation.

In this context, it is important that the recycling described and the inventive operating mode of reaction zone A make it possible to achieve therein a conversion of fresh propane to propylene with virtually one hundred percent selectivity.

The advantageousness of such a procedure exists both at lower ($\leq 30$ mol %) and at high ($\geq 30$ mol %) dehydrogenation conversions (based on single pass through reaction zone A). Generally, it is favorable in the case of the invention when the hydrogen content in reaction gas mixture input stream A is in an at least stoichiometric ratio (based on oxygen combustion to water) to the amount of oxygen present therein.

It should also be emphasized once again here that acrylic acid is removed from a product gas mixture B obtained in accordance with the invention preferably in such a way that the product gas mixture B which has been cooled beforehand if appropriate by direct and/or indirect cooling is fractionally condensed, ascending (for example into itself), in a column comprising separating internals with side draw removal of crude acrylic acid, and/or absorbed by means of water and/or aqueous solution, as described by way of example in WO 04/035 514 and DE-A 102 43 625. The crude acrylic acid withdrawn is subsequently preferably subjected to a suspension crystallization and the acrylic acid suspension crystals which are formed are preferably removed from remaining mother liquor by means of a wash column. Advantageously, the wash liquid used is the melt of acrylic acid crystals which have been removed beforehand in the wash column. Furthermore, the wash column is preferably one having forced transport of the crystal bed. It is more preferably a hydraulic or a mechanical wash column. For specific details, the description of WO 01/77 056, WO 03/041 832 and WO 03/041 833 may be followed. In other words, preference is given to recycling mother liquor which remains into the fractional condensation (cf. also EP-A 1 015 410). The secondary component discharge is normally below the side draw of the crude acrylic acid as a purge stream.

Using only one crystallization stage, it is thus possible to obtain acrylic acid having a purity of $\geq 99.8\%$ by weight which is outstandingly suitable for producing superabsorbents based on poly-Na acrylate.

Example and comparative example (construction material: type 1.4841 stainless steel)

I. General Experimental Setup of Reaction Zone A and its Operating Mode

Figure 4:
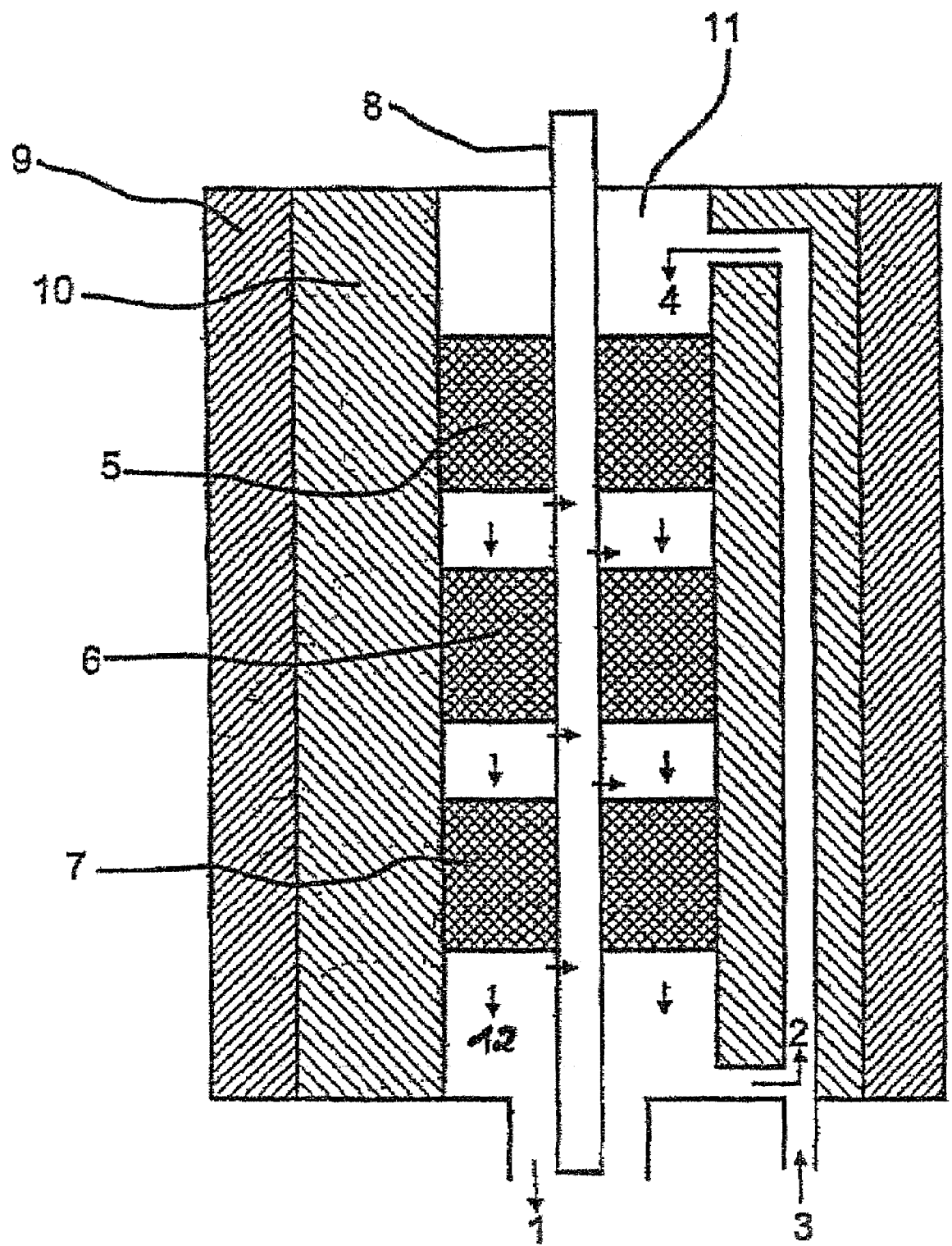

The heterogeneously catalyzed partial propane dehydrogenation is carried out in a tray loop reactor according to FIG. 4, to which the numerical addresses below relate.

A vertical tubular reactor (11) (internal diameter: 80 mm) is encased in a support heater (9) (enables substantial adiabaticity of the tubular reactor) provided with thermal insulation (10). The temperature of the support heater is 500° C. In the center of the tubular reactor is disposed a central tube (external diameter: 20 mm) which comprises a sleeve for a continuous thermal element and a sleeve for a staged thermal element. In addition, it comprises lines leading into the tubular reactor, through which reaction gas samples can be taken from the tubular reactor, and lines leading into the tubular reactor, through which air can be injected into the tubular reactor.

The tubular reactor comprises three trays (5, 6, 7) which consist of three identical beds of inert material (bed height: 100 mm; steatite spheres of diameter from 1.5 to 2.5 mm) and of a mixture (bed height: 165 mm) of dehydrogenation catalyst and steatite spheres (diameter from 1.5 to 2.5 mm) in a bed volume ratio of 1:1 (arranged in flow direction in the sequence specified) placed on a stainless steel wire mesh. The total bed height is thus in each case 265 mm.

The dehydrogenation catalyst is a Pt/Sn alloy which has been promoted with the elements Cs, K and La in oxidic form and which has been applied to the outer and inner surface of $ZrO_2 \cdot SiO_2$ mixed oxide support extrudates (mean length (Gaussian distribution in the range from 3 to 12 mm with maximum at approx. 6 mm): 6 mm, diameter: 2 mm) in the elemental stoichiometry (mass ratios including support) of $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in Example 4 of DE-A 10219879).

Upstream of each catalyst tray is mounted a mixing element. The product gas mixture A leaving the last tray (12) is divided into two halves of identical composition. One half (2) is (product gas mixture A substream 1) recycled into the dehydrogenation as a constituent of reaction gas mixture input stream A (4). The other half (1) is (product gas mixture A substream 2) conducted out of the dehydrogenation zone (reaction zone A).

Reaction gas mixture input stream A (4) consists of the gaseous starting stream 1 (2) and of the gaseous starting mixture stream (3) which is composed of steam, residual gas from the partial oxidation, fresh propane and molecular hydrogen. This starting mixture stream (3) is the motive jet of a jet pump which divides product gas mixture stream A (12) as described and generates reaction gas mixture input stream A (4).

The loading on the total amount of catalyst (calculated without inert material) on all trays with propane is always 350 l (STP)/l·h.

The entrance pressure of reaction gas mixture input stream A is 2.3 bar. Its temperature is 500° C. The pressure drop over the dehydrogenation reactor is approx. 200 mbar. Upstream of (in each case before the mixing element) the second and upstream of the third catalyst bed (in flow direction), air (500° C., reaction pressure) is injected into the reaction gas mixture. The amount is such that the highest temperature in the downstream catalyst bed in each case is from 575 to 580° C.

II. General Experimental Setup of the Heterogeneously Catalyzed Two-stage Partial Oxidation of Propylene to Acrylic Acid and its Operating Mode Experimental Arrangement First Reaction Stage:

A reaction tube (V2A steel; external diameter 30 mm, wall thickness 2 mm, internal diameter 28 mm, length: 350 cm, and also a thermal tube (external diameter 10 mm), centered in the middle of the reaction tube, to accommodate a thermoelement with which the temperature in the reaction tube can be determined for its entire length) is charged from top to bottom as follows:

Section 1: Length 50 cm Steatite rings of geometry 7 mm×7 mm×4 mm (external diameter×length×internal diameter) as a preliminary bed.

Section 2: Length 140 cm Catalyst charge of a homogeneous mixture of 20% by weight (alternatively 30% by weight) of steatite rings of geometry 5 mm×3 mm×2 mm (external diameter×length×internal diameter) and 80% by weight (alternatively 70% by weight) of unsupported catalyst from section 3.

Section 3: Length 160 cm Catalyst charge of annular (5 mm×3 mm×2 mm=external diameter×length×internal diameter) unsupported catalyst according to Example 1 of DE-A 10046957 (stoichiometry: $[Bi_2W_2O_9 \cdot 2WO_3]_{0.5}[Mo_{12}CO_{5.5}Fe_{2.94}Si_{1.59}K_{0.08}O_x]_1$). Alternatively, it is also possible here to use one of the catalysts EUC1 to EUC11 from Research Disclosure No. 497012 of Aug. 29, 2005.

From top to bottom, the first 175 cm are thermostated by means of a salt bath A pumped in countercurrent. The second 175 cm are thermostated by means of a salt bath B pumped in countercurrent.

Second Reaction Stage:

A reaction tube (V2A steel; external diameter 30 mm, wall thickness 2 mm, internal diameter 28 mm, length: 350 cm, and also a thermal tube (external diameter 10 mm), centered in the middle of the reaction tube, to accommodate a thermoelement with which the temperature in the reaction tube can be determined for its entire length) is charged from top to bottom as follows:

Section 1: Length 20 cm Steatite rings of geometry 7 mm×7 mm×4 mm (external diameter×length×internal diameter) as a preliminary bed.

Section 2: Length 90 cm Catalyst charge of a homogeneous mixture of 25% by weight (alternatively 30% by weight) of steatite rings of geometry 7 mm×3 mm×4 mm (external diameter×length×internal diameter) and 75% by weight (alternatively 70% by weight) of coated catalyst from section 4.

Section 3: Length 50 cm Catalyst charge of a homogeneous mixture of 15% by weight (alternatively 20% by weight) of steatite rings of geometry 7 mm×3 mm×4 mm (external diameter×length×internal diameter) and 85% by weight (alternatively 80% by weight) of coated catalyst from section 4.

Section 4: Length 190 cm Catalyst charge of annular (7 mm×3 mm×4 mm=external diameter×length×internal diameter) coated catalyst according to Preparation Example 5 of DE-A 10046928 (stoichiometry: $Mo_{12}V_3W_{1.0}Cu_{2.4}O_x$).

From top to bottom, the first 175 cm are thermostated by means of a salt bath C pumped in countercurrent. The second 175 cm are thermostated by means of a salt bath D pumped in countercurrent.

III. Process for Preparing Acrylic Acid from Propane (the Steady Operating State is Described) in a New Pilot Plant A reaction gas mixture input stream A which has the following contents (% by volume based on overall gas) is fed to the first catalyst bed of a tray reactor as described in I:

|  | % by volume |
|---|---|
| acrylic acid | 0.01 |
| acetic acid | 0.015 |
| water | 9.23 |
| 1-butene | 0.01 |
| isobutene | 0.02 |
| propane | 18.46 |
| propylene | 3.98 |
| ethane | 1.16 |
| ethylene | 0.22 |
| $CO_2$ | 2.34 |
| CO | 0.26 |
| $N_2$ | 59.7 |
| $O_2$ | 1.62 |
| $CH_4$ | 0.12 |
| $H_2$ | 2.83 |

It is obtained (it comprises) from (in the sequence of residual gas (23° C., 3.1 bar), fresh propane (25° C., 4 bar), hydrogen (25° C., 8 bar), steam (200° C., 2.5 bar), dehydrogenation cycle gas (600° C., 1.9 bar)):

41.9% by volume of residual gas from the partial oxidation (gaseous starting stream 2) which has the following contents:

|  | % by volume |
|---|---|
| acrylic acid | 0.02 |
| acetic acid | 0.04 |
| $H_2O$ | 2.73 |
| isobutene | 0.01 |
| acrolein | 0.05 |
| propane | 17.30 |
| propylene | 0.32 |
| ethane | 1.20 |
| ethylene | 0.22 |
| $CO_2$ | 2.41 |
| CO | 0.61 |
| $N_2$ | 71.21 |
| $O_2$ | 3.87 |

3.9% by volume of fresh propane (gaseous starting stream 3) which has the following contents:

|  | % by volume |
|---|---|
| propane | 98.91 |
| isobutane | 0.05 |
| propylene | 0.1 |
| ethane | 0.92 |
| ethylene | 0.01 |

1.02% by volume of molecular hydrogen (gaseous starting stream 4)

2.03% by volume of steam (gaseous starting stream 5) and 51.15% by volume of dehydrogenation cycle gas (product gas mixture A substream 1 or gaseous starting stream 1)

Residual gas, fresh propane, hydrogen and steam are combined in the sequence specified to give the motive jet mixture stream and brought to 500° C., 2.3 bar by indirect heat exchange with product gas mixture A substream 2.

The resulting product gas mixture A substream 2 has the following contents:

|  | % by volume |
|---|---|
| $H_2O$ | 11.84 |
| isobutene | 0.01 |
| propane | 14.32 |
| propylene | 7.52 |
| ethane | 1.21 |
| ethylene | 0.26 |
| $CO_2$ | 2.61 |
| $N_2$ | 58.41 |
| $O_2$ | 0.23 |
| $H_2$ | 3.55 |

The propane and propylene present in product gas mixture A substream 2 is removed absorptively by absorption in PKWF 4/7 af technical-grade tetradecane from Haltermann, Germany as the absorbent, and stripped by means of air to free it therefrom (the procedure is as described in DE-A 10 2004 032 129) to obtain the following charge gas for the partial oxidation which has the following contents:

|  | % by volume |
|---|---|
| $H_2O$ | 2.39 |
| tetradecane | 0.01 |
| isobutene | 0.01 |
| propane | 15.15 |
| propylene | 7.95 |
| ethane | 1.10 |
| ethylene | 0.20 |
| $CO_2$ | 1.05 |
| $N_2$ | 56.99 |
| $O_2$ | 15.16 |

This charge gas mixture (it lies outside the explosion range) is used to charge the first partial oxidation reaction stage described. The propylene loading on the fixed bed catalyst charge is selected at 185 l (STP)/l·h. The pressure at the entrance to the first reaction stage is 3.1 bar. $T_A=322°$ C.; $T_B=328°$ C.

The product gas mixture leaving the first reaction stage has the following contents:

|  | % by volume |
|---|---|
| acrylic acid | 0.46 |
| acetic acid | 0.14 |
| $H_2O$ | 10.65 |
| 1-butene | 0.01 |
| acrolein | 6.99 |
| propane | 15.16 |
| propylene | 0.17 |
| ethane | 1.10 |
| ethylene | 0.20 |
| $CO_2$ | 1.62 |
| CO | 0.23 |
| $N_2$ | 57.02 |
| $O_2$ | 6.25 |

$C^P_A$, the propene conversion at the end of reaction zone A, is 64.5 mol %.

$C^P_B$, the propene conversion at the end of reaction zone B, is 94.9 mol %.

Sufficient air (25° C.) is metered to the product gas mixture of the first stage that the molar $O_2$:acrolein ratio in the resulting mixture is 1.25.

This mixture is then used directly to charge the second reaction stage (T=231.7° C.). The acrolein loading on the fixed catalyst bed is 152 l (STP)/l·h.

$T_C$=263° C.; $T_D$=269° C. The pressure at the entrance to the second reaction stage is 2.1 bar.

The product gas mixture leaving the second reaction stage has the following contents:

|  | % by volume |
| --- | --- |
| acrylic acid | 6.72 |
| acetic acid | 0.22 |
| $H_2O$ | 11.06 |
| formaldehyde | 0.14 |
| acrolein | 0.05 |
| formic acid | 0.03 |
| maleic anhydride | 0.06 |
| benzoic acid | 0.01 |
| propane | 14.62 |
| propylene | 0.28 |
| ethane | 1.02 |
| ethylene | 0.18 |
| $CO_2$ | 2.03 |
| CO | 0.52 |
| $N_2$ | 59.86 |
| $O_2$ | 3.20 |
| propionic acid | 0.0032 |

$C^A_C$, the acrolein conversion at the end of reaction zone C, is 68.1 mol %.

$C^A_D$, the acrolein conversion at the end of reaction zone D, is 99.3 mol %.

In both reaction stages, the reaction gas mixture flows through the two catalyst tubes from the top downward.

The contents are analyzed by means of gas chromatography analysis.

The acrylic acid is removed from the product gas mixture as in the exemplary embodiments of DE-A 10 2004 032 129 and the residual gas is recycled into the heterogeneously catalyzed dehydrogenation as the gaseous starting stream 2.

The process may also be carried out as described, but with the difference that each catalyst tray in reaction zone A is only charged with the same amount of dehydrogenation catalyst, i.e. without additional use of inert material for dilution purposes.

IV. Change in the Process According to III. with Increasing Operating Time

With increasing operating time of the pilot plant, the propylene content in product gas mixture stream A falls even when the dehydrogenation catalyst is regenerated or replaced by a freshly produced charge.

At the same time, a decrease in the maximum temperature in the first fixed catalyst bed (in flow direction) of the tray reactor is detectable.

With generation of the motive jet mixture stream in the sequence of residual gas, fresh propane, steam (then indirect heat exchange) and only then molecular hydrogen, it is possible to restore the original results in new operation.

What is claimed is:

1. A process for preparing acrolein or acrylic acid or a mixture thereof from propane, comprising:

A) feeding a reaction gas mixture input stream A which has been obtained by combining at least four different gaseous starting streams 1, 2, 3 and 4 with the proviso that the three gaseous starting streams 1, 2 and 3 comprise propane, gaseous starting stream 4 is molecular hydrogen and gaseous starting stream 3 is fresh propane to the inlet into a first reaction zone A;

conducting the reaction gas mixture input stream A in reaction zone A through at least one catalyst bed, optionally with supply of further gas streams, over which a product gas mixture stream A comprising propane and propylene is formed by partial heterogeneously catalyzed dehydrogenation of propane;

conducting the product gas mixture stream A out of the first reaction zone A by discharge therefrom;

dividing the product gas mixture stream A into two product gas mixture A substreams 1 and 2 with identical composition;

recycling product gas mixture A substream 1, in a first cycle gas method, into the first reaction zone A as the gaseous starting stream 1;

optionally conducting product gas mixture A substream 2 into a first separating zone A in order to remove therefrom a portion or more of the constituents other than propane and propylene present therein to generate a remaining product gas mixture stream A' comprising propane and propylene;

B) conducting product gas mixture stream A substream 2 or product gas mixture stream A' into a secondary reaction zone B to charge at least one oxidation reactor and, in the at least one oxidation reactor, the propylene present in product gas mixture A substream 2 or in product gas mixture stream A' is subjected to a selective heterogeneously catalyzed partial gas phase oxidation with molecular oxygen to give a product gas mixture stream B comprising acrolein or acrylic acid or a mixture thereof as the target product, unconverted propane, excess molecular oxygen and optionally unconverted propylene;

conducting product gas mixture stream B out of reaction zone B into a second separating zone B;

removing target product present in product gas mixture stream B and, from the remaining residual gas comprising unconverted propane molecular oxygen and optionally unconverted propylene;

recycling at least a portion comprising unconverted propane, molecular oxygen and any unconverted propylene, in a second cycle gas method, into reaction zone A as the gaseous starting stream 2 with the proviso that gaseous starting streams 2, 3 and 4 and any additional gaseous starting streams other than gaseous starting stream 1 are combined to give a gaseous motive jet mixture stream, and a jet pump which comprises a motive nozzle, a mixing zone, a diffuser and a suction nozzle is subsequently operated with the gaseous motive jet mixture stream as the motive jet, the conveying direction of the motive jet decompressed through the motive nozzle via the mixing zone and the diffuser pointing into the inlet of the first reaction zone A and the suction direction of the suction nozzle in the direction of the outlet conducting product gas mixture stream A of the first reaction zone A, and the reduced pressure generated in the suction nozzle, with division of product gas mixture stream A into the two substreams 1 and 2, sucks in product gas mixture A substream 1 and transports it through the mixing zone via the diffuser with simultaneous mixing it with the motive jet; and releasing the reaction gas mixture input stream A formed in this way into the inlet of the first reaction zone A, wherein gaseous starting streams 2 and 3 and any additional gaseous starting streams other than gaseous streams 1 and 4 are first combined in any sequence to give a gaseous starting mixture stream and gaseous starting stream 4 is only then added to the gaseous starting mixture stream to form the gaseous motive jet mixture stream.

2. The process according to claim 1, wherein reaction gas mixture input stream A comprises five different gaseous starting streams 1, 2, 3, 4 and 5 wherein gaseous starting stream 5 is steam.

3. The process according to claim 2, wherein the gaseous starting streams other than gaseous starting streams 1 and 4 are combined to give the gaseous starting mixture stream in the sequence of gaseous starting stream 2, gaseous starting stream 5 and then gaseous starting stream 3.

4. The process according to claim 1, wherein not more than 30 seconds elapse from the time of formation of the motive jet mixture stream to the time at which reaction gas mixture input stream A reaches the first catalyst bed of reaction zone A in flow direction.

5. The process according to claim 1, wherein not more than 10 seconds elapse from the time of formation of the motive jet mixture stream to the time at which reaction gas mixture input stream A reaches the first catalyst bed of reaction zone A in flow direction.

6. The process according to claim 1, wherein reaction zone A is a tray reactor.

7. The process according to claim 1, wherein the partial heterogeneously catalyzed dehydrogenation of propane is effected autothermally in reaction zone A.

* * * * *